(12) United States Patent
Hornung et al.

(10) Patent No.: US 12,059,657 B2
(45) Date of Patent: *Aug. 13, 2024

(54) HEMODIALYZER FOR BLOOD PURIFICATION

(71) Applicant: GAMBRO LUNDIA AB, Lund (SE)

(72) Inventors: Markus Hornung, Nehren (DE); Bernd Krause, Rangendingen (DE); Markus Storr, Filderstadt (DE); Philipp Herbst, Mossingen (DE); Arnd Wochner, Dotternhausen (DE); Adriana Boschetti-De-Fierro, Hechingen (DE); Manuel Voigt, Hechingen (DE); Carina Zweigart, Schomberg (DE); Joachim Loercher, Mossingen (DE); Reinhold Buck, Alleshausen (DE); Heinrich Behr, Hechingen (DE); Werner Beck, Rottenburg (DE)

(73) Assignee: GAMBRO LUNDIA AB, Lund (SE)

( * ) Notice: Subject to any disclaimer, the term of this patent is extended or adjusted under 35 U.S.C. 154(b) by 0 days.

This patent is subject to a terminal disclaimer.

(21) Appl. No.: 18/143,324

(22) Filed: May 4, 2023

(65) Prior Publication Data

US 2023/0271146 A1 Aug. 31, 2023

Related U.S. Application Data

(63) Continuation of application No. 17/590,097, filed on Feb. 1, 2022, now Pat. No. 11,666,869, which is a continuation of application No. 16/851,439, filed on Apr. 17, 2020, now Pat. No. 11,273,417, which is a continuation of application No. 15/115,951, filed as application No. PCT/EP2015/052365 on Feb. 5, 2015, now Pat. No. 10,661,230.

(30) Foreign Application Priority Data

Feb. 6, 2014 (EP) .................................... 14154172

(51) Int. Cl.
| | | |
|---|---|---|
| A61M 1/34 | (2006.01) | |
| B01D 61/24 | (2006.01) | |
| B01D 63/02 | (2006.01) | |
| B01D 69/08 | (2006.01) | |
| B01D 71/38 | (2006.01) | |
| B01D 71/44 | (2006.01) | |
| B01D 71/68 | (2006.01) | |

(52) U.S. Cl.
CPC ........... *B01D 71/68* (2013.01); *A61M 1/3479* (2014.02); *B01D 61/243* (2013.01); *B01D 63/0233* (2022.08); *B01D 69/084* (2013.01); *B01D 69/087* (2013.01); *B01D 71/381* (2022.08); *B01D 71/441* (2022.08); *B01D 2323/06* (2013.01); *B01D 2323/12* (2013.01); *B01D 2325/022* (2013.01); *B01D 2325/20* (2013.01)

(58) Field of Classification Search
CPC ..... B01D 61/243; B01D 2325/20; A61M 1/16
See application file for complete search history.

(56) References Cited

U.S. PATENT DOCUMENTS

| | | | |
|---|---|---|---|
| 5,891,338 A | 4/1999 | Bell et al. | |
| 5,938,929 A | 8/1999 | Shimagaki et al. | |
| 7,875,183 B2 | 1/2011 | Bradwell et al. | |
| 9,617,421 B2 | 4/2017 | Ford et al. | |
| 2006/0234582 A1 | 10/2006 | Gohl et al. | |
| 2010/0084339 A1 | 4/2010 | Hutchison et al. | |
| 2012/0074063 A1 | 3/2012 | Krause et al. | |
| 2012/0074064 A1 | 3/2012 | Krause et al. | |
| 2012/0305487 A1 | 12/2012 | Beck et al. | |
| 2013/0338297 A1 | 12/2013 | Ford et al. | |
| 2017/0165615 A1 | 6/2017 | Hornung et al. | |
| 2020/0316533 A1 | 10/2020 | Behr et al. | |
| 2022/0152562 A1 | 5/2022 | Loercher et al. | |

FOREIGN PATENT DOCUMENTS

| | | |
|---|---|---|
| EP | 0168783 A1 | 1/1986 |
| EP | 0305687 A1 | 3/1989 |
| EP | 0844015 A2 | 5/1998 |
| EP | 1388364 A1 | 2/2004 |
| EP | 1671695 A1 | 6/2006 |
| EP | 1710011 A1 | 10/2006 |
| EP | 2113298 A1 | 11/2009 |
| EP | 2161072 A1 | 3/2010 |
| EP | 2216060 A1 | 8/2010 |
| EP | 2243367 A2 | 10/2010 |
| EP | 2253367 A1 | 11/2010 |
| EP | 2281625 A1 | 2/2011 |
| EP | 2815807 A1 | 12/2014 |

(Continued)

OTHER PUBLICATIONS

Granath et al., "Molecular weight distribution analysis by gel chromatography on sephadex", J Chromatogr A. 1967;28 (C): 69-81.

(Continued)

*Primary Examiner* — Bradley R Spies
(74) *Attorney, Agent, or Firm* — Barnes & Thornburg LLP

(57) ABSTRACT

The present disclosure relates to a dialyzer comprising a bundle of semipermeable hollow fiber membranes which is suitable for blood purification, wherein the dialyzer has an increased ability to remove larger molecules while at the same time it is able to effectively remove small uremic toxins and efficiently retain albumin and larger proteins. The invention also relates to using said dialyzer in hemodialysis.

20 Claims, 13 Drawing Sheets

(56) References Cited

FOREIGN PATENT DOCUMENTS

| | | |
|---|---|---|
| EP | 3102312 | 8/2015 |
| EP | 3102314 | 8/2015 |
| GB | 2009034 A | 6/1979 |
| JP | 0970524 A | 3/1997 |
| JP | 2010233980 A | 10/2010 |
| WO | 09637282 A1 | 11/1996 |
| WO | 0160477 A2 | 8/2001 |
| WO | 2004056460 A1 | 7/2004 |
| WO | 2010133612 A1 | 11/2010 |
| WO | 2010133614 A1 | 11/2010 |
| WO | 2010133615 A1 | 11/2010 |
| WO | 2012164019 A1 | 12/2012 |
| WO | 2013190022 A1 | 12/2013 |
| WO | 2015118045 A1 | 8/2015 |
| WO | 2015118046 A1 | 8/2015 |

OTHER PUBLICATIONS

Michaels, "Analysis and Prediction of Sieving Curves for Ultrafiltration Membranes: A Universal Correlation?", Sep. Sci. Technol. 1980; 15(6): 1305-1322.

Wienk, "A new spinning technique for hollow fiber ultrafiltration membranes" J of Membrane Science, 1993; 78:93-100.

Wienk, "Ultrafiltration membranes from a polymer blend: hollow fiber preparation and characterization," Thesis Enchede, The Netherlands (Chapter 1), 1993; ISBN 0-9006058-8.

Wienk, "Spinning of hollow fiber ultrafiltration membranes from a polymer blend," Journal of Membrane Science, 1995; 106:233-243.

Kunas et al., "The effect of blood contact and reuse on the transport properties of high-flux dialysis membranes", ASAIO J. 1996; 42(4): 288-294.

Leypoldt et al., "Characterization of molecular transport in artificial kidneys", Artif Organs. 1996; 20(5): 381-389.

Mulder, Basic Principles of Membrane Technology, Kluwer Academic Publisher, 1996; ISBN 0-7923-4247-X.

Krause, "Polymeric membranes for medical applications," Chemie Ingenier Technik, 2003; 75(11):1725-1732.

Uhlenbusch-Kower, "Understanding membranes and dialyzers," Pabst Science Publishers, 2004; ISBN 3-89967-005-1.

Ward, "Protein leaking membranes for hemodialysis, a new class of membranes in search of an application" Journal of the American Society of Nephrology, 2005; 16(8):2421-2430.

Annex 1 submitted in support of EP 15702769.9 1 3102312 Opposition, Jun. 26, 2019.

Yang, "Tailoring pore size and pore size distribution of kidney dialysis hollow fiber membranes via dual-bath coagulation approach," Journal of Membrane Science, 2007; 290:153-163.

Bakhshayeshi et al., "Dextran sieving test for characterization of virus filtration membranes", J. Membr. Sci. 2011; 379(1-2): 239-248.

Bakhshayeshi et al., "Understanding dextran retention data for hollow fiber ultrafiltration membranes", J. Membr. Sci. 2011: 385-386(1): 243-250.

Hwang et al., "Effect of membrane pore size on the performance of cross-flow microfiltration of BSA/dextran mixtures", J Membr Sci. 2011; 378(1-2): 272-279.

Peeva et al., "Factors affecting the sieving behavior of anti-fouling ultrafiltration membranes", J Membr Sci. 2012; 390-391: 99-112.

Boschetti-De-Fierro, A., et al., "Extended Characterization of a New Class of Membranes for Blood Purification," Jul. 1, 2013, International Journal of Artificial Organs, vol. 36, Nr: 7, pp. 455-463. (Abstract Only.

Boschetti-De-Fierro, "Extended characterization of a new class of membranes for blood purification the high cut-off membranes," Int J Artif Organs, 2013; 36(7): 455-463.

PCT Search Report and Written Opinion for PCT/EP2015/052364, completed Apr. 1, 2015.

Hulko, "Requirements and pitfalls of dialyzer sieving coefficients comparisons," Artificial Organs, 2018:1-10.

Communication of a notice of opposition submitted in support of EP 15702768.1 / 3102314 Opposition, Jul. 1, 2019 (including English translations).

Communication of a notice of opposition submitted in support of EP 15702769.9 1 3102312 Opposition, Jul. 4, 2019.

Notice of opposition letter submitted in support of EP 15702768.1 / 3102314 Opposition, Jun. 19, 2019 (including English translations).

Notice of opposition letter submitted in support of EP 15702769.9 1 3102312 Opposition, Jun. 26, 2019.

Notice of opposition submitted in support of EP 15702768.1 / 3102314 Opposition, Jun. 19, 2019.

Notice of opposition submitted in support of EP 15702769.9 1 3102312 Opposition, Jun. 26, 2019.

Vanholder et al., Review on uremic toxins: Classification, concentration, and interindividual variability ", Kidney Int." (2003)63, 1934-1943.

Annex 2 submitted in support of EP 15702769.9 1 3102312 Opposition, Jun. 26, 2019.

Annex 1 submitted in support of EP 15702768.1 / 3102314 Opposition, Jun. 19, 2019.

HEMODIALYZER FOR BLOOD PURIFICATION

CROSS-REFERENCE TO RELATED APPLICATIONS

This application is a continuation application of U.S. patent application Ser. No. 17/590,097, filed on Feb. 1, 2022, which is a continuation application of U.S. patent application Ser. No. 16/851,439, filed on Apr. 17, 2020, which is a continuation application of U.S. patent application Ser. No. 15/115,951, filed on Aug. 2, 2016, which is the U.S. national phase of PCT/EP2015/052365, filed on Feb. 5, 2015, which claims priority to European Patent Application 14154172.2, filed on Feb. 6, 2014. The disclosures of U.S. patent application Ser. No. 17/590,097, U.S. patent application Ser. No. 16/851,439, U.S. patent application Ser. No. 15/115,951, European Patent Application 14154172.2, and PCT/EP2015/052365 are hereby incorporated herein by reference in their entireties.

TECHNICAL FIELD

The present disclosure relates to a dialyzer comprising a bundle of semipermeable hollow fiber membranes which is suitable for blood purification, wherein the dialyzer has an increased ability to remove larger molecules while at the same time it is able to effectively remove small uremic toxins and efficiently retain albumin and larger proteins. The invention also relates to using said dialyzer in hemodialysis.

DESCRIPTION OF THE RELATED ART

Capillary dialyzers are widely used for blood purification in patients suffering from renal insufficiency, i.e., for treatment of the patients by hemodialysis, hemodiafiltration or hemofiltration.

The devices generally consist of a casing comprising a tubular section with end caps capping the mouths of the tubular section. A bundle of hollow fiber membranes is arranged in the casing in a way that a seal is provided between the first flow space formed by the fiber cavities and a second flow space surrounding the membranes on the outside. Examples of such devices are disclosed in EP 0 844 015 A2, EP 0 305 687 A1, and WO 01/60477 A2.

Module performance is controlled by membrane properties and mass transfer boundary layers that develop in the fluid adjacent to the membrane surface in the lumen and the shell. Boundary layer resistances are significant in many processes including dialysis.

Accordingly, the most important factor influencing performance of the device is the hollow fiber membrane which is used for accomplishing the device. Dialysis membranes today are designed to allow for the removal of uremic toxins and excess water from the blood of patients with chronic renal failure while balancing the electrolyte content in the blood with the dialysis fluid. Uremic toxins can be classified according to their size as shown in FIG. 1 or as described in Vanholder et al.: "Review on uremic toxins: Classification, concentration, and interindividual variability", Kidney Int. (2003) 63, 1934-1943, and/or according to their physicochemical characteristics in small watersoluble compounds (e.g., urea and creatinine), proteinbound solutes (e.g., p-cresyl sulfate) and middle molecules (e.g., b2-microglobulin and interleukin-6). While the removal of small molecules takes place mainly by diffusion due to concentration differences between the blood stream and the dialysis fluid flow, the removal of middle molecules is mainly achieved by convection through ultrafiltration. The degree of diffusion and convection depends on the treatment mode (hemodialysis, hemofiltration or hemodiafiltration) as well as on the currently available membrane type (low-flux high-flux, protein leaking, or high cut-off membranes).

Another important factor influencing performance of the device depends strongly on the geometry of the housing and the fiber bundle located therein, including the geometry of the single hollow fibers. Relevant parameters as concerns the fibers are, apart from their specific membrane structure, composition and related performance the effective (accessible) length of the fibers, the inner diameter and the wall thickness of the fibers and their overall threedimensional geometry. The aforementioned concentration and thermal boundary layers adjacent to the fiber surface as well as uniformity of the flow through a dialyzer will otherwise be influenced by the packing density and/or the crimping of the single hollow fibers. Crimping or undulation transforms a straight fiber into a generally wavy fiber. Crimped fibers overcome problems of uniformity of flow around and between the fibers and of longitudinal fiber contact which can reduce the fiber surface area available for mass transfer by reducing said longitudinal contact between adjacent fibers, thereby improving flow uniformity and access to membrane area. The performance of dialyzers is related also to the membrane packing density which in turn is closely connected to the flow characteristics. A high membrane packing density increases the performance of the device as long as the uniformity of the flow is not affected. This can be achieved by introducing, into the housing, fiber bundles with fibers that are at least partially crimped. For example, EP 1 257 333 A1 discloses a filter device, preferably for hemodialysis, that consists of a cylindrical filter housing and a bundle of hollow fibers arranged in the filter housing, wherein all of the hollow fibers are crimped, resulting in a wavelength and amplitude which follow a certain geometrical principle wherein also fibers length, outer fiber diameter and the diameter of the fiber bundle play some role. The packing density of the fibers within the housing is in the range of from 60.5 to 70*, relative to the usable cross-section area of the housing which is calculated by multiplying the cross-section area by 0.907. EP 2 815 807 A1 refers to dialyzers comprising crimped fibers, wherein only a specific portion of the fibers is crimped, which leads to some further improvements of the filter performance.

The sieving property of a membrane, i.e. its permeability to solutes, is determined by the pore size and sets the maximum size for the solutes that can be dragged through the membrane with the fluid flow. The sieving coefficient for a given substance could be simply described as the ratio between the substance concentration in the filtrate and its concentration in the feed (i.e., the blood or plasma), and is therefore a value between 0 and 1. Assuming that the size of a solute is proportional to its molecular weight, a common way to illustrate the properties of membranes is by building a sieving curve, which depicts the sieving coefficient as a function of the molecular weight. The expression "molecular weight cut-off" or "MWCO" or "nominal molecular weight cut-off" as interchangeably used herein is a value for describing the retention capabilities of a membrane and refers to the molecular mass of a solute where the membranes have a rejection of 90%, corresponding to a sieving coefficient of 0.1. The MWCO can alternatively be described as the molecular mass of a solute, such as, for example, dextrans or proteins where the membranes allow passage of 10% of the molecules. The shape of the curve depends, to a significant extent, on the pore size distribution and to the physical form of appearance of the membrane and its pore structure, which can otherwise be only inadequately described. Sieving coefficients therefore are a good description not only of the performance of a membrane but are also descriptive of the specific submacroscopic structure of the membrane.

In vitro characterization of blood purification membranes includes the determination of the removal rate for small and middle molecules as well as for albumin. For this purpose, filtration experiments are carried out with different marker solutes, among which dextran has been widely used since it is non-toxic, stable, inert and available in a wide range of molecular weights (Michaels A S. Analysis and Prediction of Sieving Curves for Ultrafiltration Membranes: A Universal Correlation? *Sep Sci Technol.* 1980; 15(6):1305-1322. Leypoldt J K, Cheurig A K. Characterization of molecular transport in artificial kidneys. *Artif Organs.* 1996; 20 (5): 381-389). Since dextrans are approximately linear chains, their size does not correspond to that of a protein with similar molecular weight. However, comparisons are possible once the radius of the dextran coiled chain is calculated. The sieving curve determined for a polydisperse dextran mixture can thus be considered a standard characterization technique for a membrane, and a number of recent publications have analyzed this methodology (Bakhshayeshi M, Kanani D M, Mehta A, et al. Dextran sieving test for characterization of virus filtration membranes. *J Membr Sci.* 2011; 379 (1-2):239-248. Bakhshayeshi M, Zhou H, Olsen C, Yuan W, Zydney A L. Understanding dextran retention data for hollow fiber ultrafiltration membranes. *J Membr Sci.* 2011; 385-386(1):243-250. Hwang K J, Sz P Y. Effect of membrane pore size on the performance of cross-flow microfiltration of BSA/dextran mixtures. *J Membr Sci.* 2011; 378 (1-2):272-279. 11. Peeva P D, Million N, Ulbricht M. Factors affecting the sieving behavior of anti-fouling thin-layer cross-linked hydrogel polyethersulfone composite ultrafiltration membranes. *J Membr Sci.* 2012; 390-391:99-112. Boschetti-de-Fierro A et al. Extended characterization of a new class of membranes for blood purification: The high cut-off membranes. *Int J Artif Organs* 2013; 36(7), 455-463).

Conventional dialysis membranes are classified as low-flux or high-flux, depending on their permeability. A third group, called protein leaking membranes, is also available on some markets. These three membrane groups were described in a review by Ward in 2005 (Ward R A. Protein-leaking membranes for hemodialysis: a new class of membranes in search of an application? *J Am Soc Nephrol.* 2005; 16(8):2421-2430). High-flux membranes used in devices, such as, for example, Polyflux® 170H (Gambro), Revaclear® (Gambro), Ultraflux® EMIC2 (Fresenius Medical Care), Optiflux® F180NR (Fresenius Medical Care) have been on the market for several years now. The high-flux membranes used therein are mainly polysulfone or polyethersulfone based membranes and methods for their production have been described, for example, in U.S. Pat. No. 5,891,338 and EP 2 113 298 A1. Another known membrane is used in the Phylther® HF 17G filter from Bellco Societa unipersonale a r.l. It is generally referred to as high-flux membrane and is based on polyphenylene. In polysulfone or polyethersulfone based membranes, the polymer solution often comprises between 10 and 20 weight-n of polyethersulfone or polysulfone as hydrophobic polymer and 2 to 11 weight-% of a hydrophilic polymer, in most cases PVP, wherein said PVP generally consists of a low and a high molecular PVP component. The resulting high-flux type membranes generally consist of 80-99% by weight of said hydrophobic polymer and 1-20% by weight of said hydrophilic polymer. During production of the membrane the temperature of the spinneret generally is in the range of from 25-55° C. Polymer combinations, process parameters and performance data can otherwise be retrieved from the references mentioned or can be taken from publicly available data sheets. The expression "high-flux membrane(s)" as used herein refers to membranes having a MWRO between 5 kDa and 10 kDa and a MWCO between 25 kDa and 65 kDa, as determined by dextran sieving measurements according to Boschetti-de-Fierro et al. (2013). The average pore radius is in the range of from 3.5 to 5.5 nm, wherein the pore size is determined from the MWCO based on dextran sieving coefficients according to Boschetti-de-Fierro et al. (2013) and Granath et al. (1967). Molecular weight distribution analysis by gel chromatography on sephadex. *J Chromatogr A.* 1967; 28 (C):69-81. The main difference between high-flux membranes and low-flux membranes is a higher water permeability and the ability to remove small-to-middle molecules like $\beta2$-microglobulin.

High-flux membranes are also contained in current filter devices which can be used or have been explicitly designed for use in hemodiafiltration, for example the commercially available products Nephros OLpūr™ MD 190 or MD 220 (Nephros Inc., USA) or the $FX_{CorDiax}600$, $FX_{CorDiax}800$ or $FX_{CorDiax}1000$ filters (Fresenius Medical Care Deutschland GmbH). While hemodialysis (HD) is primarily based on diffusion, thus relying on differences in concentration as the driving force for removing unwanted substances from blood, hemodiafiltration (HDF) also makes use of convective forces in addition to the diffusive driving force used in HD. Said convection is accomplished by creating a positive pressure gradient across the dialyzer membrane. Accordingly, blood is pumped through the blood compartment of the dialyzer at a high rate of ultrafiltration, so there is a high rate of movement of plasma water from blood to dialysate which must be replaced by substitution fluid that is infused directly into the blood line. Dialysis solution is also run through the dialysate compartment of the dialyzer. Hemodiafiltration is used because it may result in good removal of both large and small molecular weight solutes. The substitution fluid may be prepared on-line from dialysis solution wherein the dialysis solution is purified by passage through a set of membranes before infusing it directly into the blood line. There are still some concerns as regards the on-line creation of substitution fluid because of potential impurities in the fluid. Other concerns are related to the fact that HDF therapy requires a high blood flow and a corresponding access and patients who tolerate such high flows. However, a considerable number of patients are older, diabetic and/or with a poor vascular access; in this situation high blood flows are more difficult to get at the expense of lower postdilution exchange volumes, thus limiting the usability and/or benefit of HDF treatment. Especially for these patients it would be extremely desirable to achieve an at least equally good removal of both large and small molecular weight solutes also with hemodialysis, which so far is not feasible.

Protein leaking membranes, another class of membranes which should be mentioned here, have a water permeability similar to that of low-flux membranes, the ability to remove small-to-middle molecules similar to high-flux membranes, and they show albumin loss which is generally higher than that of high-flux membranes. Their use in HDF application is therefore not advisable because especially in convective procedures, such as hemodiafiltration, their albumin leakage is too high.

Lately a fourth type has emerged, called high cut-off membranes, which form a new group in addition to the ones mentioned before. This type of membrane has first been disclosed in WO 2004/056460 A1 wherein certain early high cut-off membranes are described which were primarily intended for the treatment of sepsis by eliminating sepsisassociated inflammatory mediators. Advanced dialyzers making use of high cut-off type membranes which are currently on the market are, for example, HCO1100®, septeX™ and Theralite®, all available from Gambro Lundia AB. Known uses of said advanced high cut-off membranes include treatment of sepsis (EP 2 281 625 A1), chronic inflammation (EP 2 161 072 A1), amyloidosis and rhabdomyolysis and treatment of anemia (US 2012/0305487 A1), the most explored therapy to date being the treatment of myeloma kidney patients (U.S. Pat. No. 7,875,183 B2). Due to the loss of up to 40 g of albumin per standard treatment, high cut-off membranes so far have been used for acute applications only, although some physicians have contemplated benefits of using them in chronic applications, possibly in conjunction with albumin substitution and/or in addition to or in alternate order with standard high-flux dialyzers. The and temperature of the coagulation bath, relative to the spinning conditions for producing a high-flux membrane with about the same composition of polymers. In addition, for the production of the latest high cut-off membranes such as the Theralite® membrane, the ratio of water and solvent ($H_2O$/solvent) in the polymer solution is also slightly changed to lower values while the polymer content in said solution can otherwise be similar to or the same as used for producing high-flux membranes such as, for example, the Revaclear® membrane.

The MWCO and MWRO values used for describing the prior art membranes and the membranes according to the invention have been measured before blood or plasma contact, because the sieving properties of synthetic membranes may change after such contact. This fact can be attributed to the adhesion of proteins to the membrane surface, and is therefore related to the membrane material and the medium characteristics. When proteins adhere to the membrane surface, a protein layer is created on top of the membrane. This secondary layer acts also as a barrier for the transport of substances to the membrane, and the phenomenon is commonly referred to as fouling. The general classification and typical performance of blood purification membranes according to said reference is summarized in Table T.

TABLE I

General classification and typical performance of hemodialysis membranes

| Dialyzer type | Water permeability$^a$ ml/(m²hmmHg) | Sieveing Coefficient$^b$ | | FLC Clearance$^c$ | | Albumin Loss (g)$^d$ |
|---|---|---|---|---|---|---|
| | | β2-Microglobulin | Albumin | Kappa | Lambda | |
| Low-flux | 10-20 | — | <0.01 | — | — | 0 |
| High-flux | 200-400 | 0.7-0.8 | <0.01 | <10 | <2 | <0.5 |
| Protein leaking | 50-500 | 0.9-1.0 | 0.02-0.03 | — | — | 2-6 |
| High cutoff | 862-1436 | 1.0 | 0.1-0.2 | 14-38 | 12-33 | 22-28$^{(*)}$ |

$^a$with 0.9 wt.-% sodium chloride at 37 ± 1° C. and $Q_B$ 100-500 ml/min
$^b$according to EN1283 with $Q_B$ max and UF 20%
$^c$Serum Free Light Chains, Clearance in vitro, $Q_B$ 250 ml/min and $Q_D$ 500 ml/min, UF 0 ml/min, Bovine Plasma, 60 g/l, 37° C., Plasma Level: human κ 500 mg/l, human λ 250 mg/l. All clearances in ml/min, measured for membrane areas between 1.1 and 2.1 m²
$^d$measured in conventional hemodialysis, after a 4-h session, with $Q_B$ 250 ml/min and $Q_D$ 500 ml/min, for membrane areas between 1.1 and 2.1 m².

expression "high cut-off membrane" or "high cut-off membranes" as used herein refers to membranes having a MWRO of between 15 and 20 kDa and a MWCO of between 170-320 kDa. The membranes can also be characterized by a pore radius, on the selective layer surface of the membrane, of between 8-12 nm. For the avoidance of doubt, the determination of MWRO and MWCO for a given membrane and as used herein is according to the methods of Boschetti-de-Fierro et al. (2013); see "Materials and Methods" section of the reference and Example 3 of this description. Accordingly, the expressions "as determined by dextran sieving" or "based on dextran sieving" also refer to the dextran sieving method as described in Boschetti-de-Fierro et al. (2013) and as further described herein. Processes for producing high cut-off membranes have been described, for example, in the aforementioned references. As disclosed already in WO 2004/056460 A1, a key element for their generation is an increase in the temperature of the spinning process, i.e. the temperature of the spinneret, the spinning shaft temperature As already mentioned, sieving curves give relevant information in two dimensions: the shape of the curve describes the pore size distribution, while its position on the molecular weight axis indicates the size of the pores. The molecular weight cut-off (MWCO) limits the analysis of the sieving curve to only one dimension, namely to the size of the pores where the sieving coefficient is 0.1. To enhance membrane characterization, the molecular weight retention onset (MWRO) is used herein for characterizing the membranes according to the invention. By using both MWRO and MWCO it becomes evident how the membranes of the invention distinguish themselves from prior art membranes, for typical representatives of which MWCO and MWRO have been determined under the same conditions as for the membranes of the invention.

The MWRO is defined as the molecular weight at which the sieving coefficient is 0.9 (see FIG. 4 of Boschetti-de-Fierro et al (2013)). It is otherwise analogous to the MWCO but describes when the sieving coefficient starts to fall.

Defining two points on the sieving curves allows a better, more concise characterization of the sigmoid curve, giving an indication of the pore sizes and also of the pore size distribution and thus of the most relevant physical parameters which determine a membrane. The expression "molecular weight retention onset", "MWRO" or "nominal molecular weight retention onset" as interchangeably used herein therefore refers to the molecular mass of a solute where the membranes have a rejection of 10%, or, in other words, allow passage of 90% of the solute, corresponding to a sieving coefficient of 0.9. The dextran data from molecular weight fractions is also directly related to the size of the molecules and is an indirect measure of the pore sizes in the membranes. Thus, the MWRO is also directly related to a physical property of the membrane. One can interpret this value as some reference of where the pore size distribution starts, while the MWCO indicates where it ends.

The use of dextran sieving curves together with the respective MWCO and MWRO values based thereon allows differentiating the existing dialyzer types low-flux, high-flux, protein leaking, or high cut-off (see FIG. 5 of Boschet-tide-Fierro et al. (2013)) and the new and improved membranes which is described herein. Compared, for example, to the high-flux dialyzers, which are the standard for current dialysis treatment, the low-flux dialyzers are depicted in a group with low MWRO and MWCO (FIG. 2). The other two known families —protein leaking and high cut-off dialyzers— have different characteristics. While the protein leaking dialyzers are mainly characterized by a high MWCO and a low MWRO, the high cut-off family can be strongly differentiated due to the high in vitro values for both MWRO and MWCO (Table II).

TABLE II

General classification of current hemodialysis membranes based on dextran sieving

| Dialyzer type | Structural Characteristics | | |
|---|---|---|---|
| | MWRO [kDa] | MWCO [kDa] | Pore radius [nm] |
| Low-flux | 2-4 | 10-20 | 2-3 |
| High-flux | 5-10 | 25-65 | 3.5-5.5 |
| Protein leaking | 2-4 | 60-70 | 5-6 |
| High cut-off | 15-20 | 170-320 | 8-12 |

It is obvious from FIG. 5 of Boschetti et al. (2013) that there exists a gap between the currently known high cut-off and high-flux membranes, which so far could not be addressed by currently available membranes and dialyzers containing them.

Dialyzers comprising improved high-flux membranes which would be located in this gap are highly desirable, as they would form the nexus between an increasingly important removal of larger uremic solutes as realized in present high cut-off membranes, and a sufficient retention of albumin and other essential proteins which currently puts a limit to an even broader usability of the beneficial characteristics of high cut-off membranes, for example in chronic applications. Such hemodialyzer are also desirable as they would be able to achieve performances of prior art dialyzers used in hemodiafiltration mode, thereby avoiding the drawbacks which are connected to hemodiafiltration. However, to date, no such membranes or hemodialyzer have been described or prepared, even though continuous attempts have been made to produce such membranes (see, for example, EP 2 253 367 A1). So far, no available membrane was able to, fulfil the above described expectations as regards MWRO and MWCO. Membranes which are coming close to said gap (EP 2 253 367 A1) could be prepared only by means of processes which are not feasible for industrial production.

SUMMARY

It was the object of the present invention to develop an improved hemodialysis filter which is able to combine an efficient removal of small uremic molecules from blood with an enhanced removal of middle and large uremic solutes and an improved retention of albumin in larger proteins, which currently can be achieved, to a certain extent, only by hemodiafiltration but not by hemodialysis. In the present invention, improved hemodialyzers are disclosed which are characterized, on the one hand, by a new hollow fiber membrane having a molecular retention onset (MWRO) of between 9.0 kDa and 14.0 kDa and a molecular weight cut-off (MWCO) of between 55 kDa and 130 kDa as determined by dextran sieving curves before the membrane has had contact with blood or a blood product. On the other hand, the hemodialyzers of the invention are characterized by an improved overall design, comprising the single hollow fibers, which are characterized by inner diameters of preferably below 200 µm and a wall thickness of preferably below 40 µm. The fibers in the bundle may be crimped or the fiber bundle may consist of 80% to 95% crimped fibers and of 5% to 15% non-crimped fibers, relative to the total number of fibers in the bundle. The packing density of the hemodialyzers is in the range of from 50% to 65%. As a result of the overall design of the devices, the hemodialyzers of the invention significantly improve the removable range of uremic solutes while sufficiently retaining albumin for safe use in chronic applications with patients suffering from renal failure.

In other words, the selectivity of the hemodialyzer is significantly improved compared to dialyzers of the prior art, which becomes evident from the combined MWRO and MWCO values for the membranes according to the invention. The membranes in the context of the present invention are polysulfone-based, polyethersulfone-based or poly(aryl)ethersulfone-based synthetic membranes, comprising, in addition, a hydrophilic component such as, for example, PVP and optionally low amounts of further polymers, such as, for example, polyamide or polyurethane, and they are preferably produced without treating them with a salt solution before drying such as disclosed in EP 2 243 367 A1. The present invention is also directed to methods of using the filter devices in blood purification applications, in particular in hemodialysis methods used to treat advanced and permanent kidney failure.

BRIEF DESCRIPTION OF THE DRAWINGS

FIG. 8A shows a profile of the hollow fiber membrane, whereas FIG. 8B a close-up cross-section through the membrane, where the overall structure of the membrane is visible. FIGS. 8C and 8D represent further magnifications of the membrane wall, wherein the inner selective layer is visible. FIG. 8E shows the inner selective layer of the membrane, FIG. 8F shows the outer surface of the hollow fiber membrane.

FIG. 9A shows a profile of the hollow fiber membrane, whereas FIG. 9B a close-up cross-section through the membrane, where the overall structure of the membrane is visible. FIGS. 9C and 9D represent further magnifications of the membrane wall, wherein the inner selective layer is visible. FIG. 9E shows the inner selective layer of the membrane, FIG. 9F shows the outer surface of the hollow fiber membrane.

DETAILED DESCRIPTION

Figure 1:
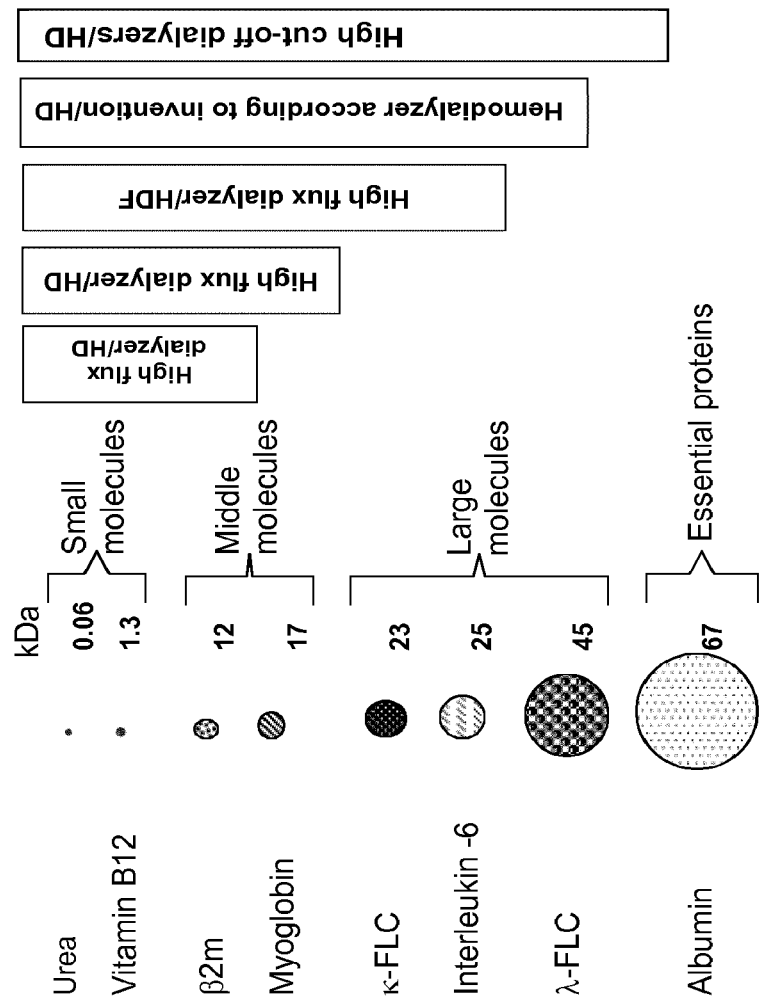
FIG. 1 is a general, schematic representation of small, middle and large molecular solutes which are removed by various blood purification membranes and operation modes in comparison. HD represents hemodialysis. HDF represents hemodiafiltration. The largest molecules will be removed by high cut-off membranes (hemodialysis mode). High-flux meiribranes, in hemodialysis mode, are able to remove small molecules and certain middle molecules in hemodialysis, whereas the same membranes will remove larger middle molecules in hemodiafiltration mode. The membranes according to the invention are able to remove also large molecules such as IL-6 and λ-FLC, comparable or superior to HDF, but in hemodialysis mode. Essential proteins like, for example, albumin are essentially retained.

Middle molecules, consisting mostly of peptides and small proteins with molecular weight the range of 500-60,000 Da, accumulate in renal failure and contribute to the uremic toxic state. These solutes are not well cleared by low-flux dialysis. High-flux dialysis will clear middle molecules, partly by internal filtration. Many observational studies over the last years have indeed supported the hypothesis that higher molecular weight toxins (FIG. 1) are responsible for a number of dialysis co-morbidities, including, for example, chronic inflammation and related cardiovascular diseases, immune dysfunctions, anaemia etc., influencing also the mortality risk of chronic hemodialysis patients. It is possible to enhance the convective component of high-flux dialysis by hemodiafiltration (HDF). However, in case of postdilution HDF, increasing blood flow above the common routine values may create problems of vascular access adequacy in many routine patients and is therefore not accessible to all patients in need. Predilution HDF allows for higher infusion and ultrafiltration rates. However, this advantage in terms of convective clearances is thwarted by dilution of the solute concentration available for diffusion and convection, resulting in the reduction of cumulative transfer. Therefore, there is an increasing interest in accomplishing filter devices which in hemodialysis mode allow an enhanced transport of middle and even large molecules and a reliable and efficient removal of small solutes such as urea, comparable or superior to high-flux membranes when used in HDF mode, while at the same time efficiently retaining albumin and larger essential proteins such as coagulation factors, growth factors and hormones. In short, such desired hemodialyzers are able to provide the best possible clearance for low and high-molecular weight uremic toxins by hemodialysis, which is at least comparable and preferably superior to the clearance of said toxins in haemodiafiltration treatments. In other words, the hemodialyzers of the invention at an average blood flow of between 200 and 600 ml/min 350-450 ml/min, a dialysate flow of between 300-1000 ml/min and an ultrafiltration rate of 0-30 ml/min are designed to provide for clearance rates determined in vitro according to ISO8637:2014 (E) for a given substance generally used to define the clearance performance of a dialyzer, such as, for example, cytochrome C or myoglobin, which are about equivalent or higher than those achieved with dialyzers comprising high flux membranes at the same $Q_B$ rate and an ultrafiltration rate of above 50 ml/min. The expression "equivalent" as used herein refers to clearance values which deviate from each other by not more than ±10%, preferably by not more than ±5%. According to one embodiment of the invention, the ultrafiltration rate used with a hemodialyzer of the invention is between 0 and 20 ml/min. According to another embodiment of the invention, the ultrafiltration rate used with a hemodialyzer of the invention is between 0 and 15 ml/min. According to yet another embodiment of the invention, the ultrafiltration rate is 0 ml/min. The blood flow range used with a hemodialyzer of the invention according to another embodiment of the invention will be in the range of between 350-450 ml/min, and the dialysate flow will be in the range of from between 500 and 800 ml/min.

If used, for example, at a blood flow of between 200-500 ml/min, a dialysate flow of between 500-800 ml/min and an ultrafiltration rate of between 0 and 30 ml/min the albumin loss per treatment (240 min±20%) with a hemodialysis filter according to the invention is limited to a maximum of 7 g. According to one aspect of the present invention, the albumin loss under the same conditions is limited to 4 g, see also Example 5.

In the context of the present invention, the expressions "hemodialyzer (s)", "hemodialysis device", "hemodialysis filter", "filter for hemodialysis" or "filter device for hemodialysis" are used synonymously and refer to the devices according to the invention as described herein. The expression "hemodiafilter(s)" as used herein refers to filter devices which can be used or are preferably used in blood treatments performed in hemodiafiltration methods for blood purification. The expressions "dialyzer", "dialysis filter", "filter" or "filter device", if not indicated otherwise, generally refer to devices which can be used for blood purification.

The expression "hemodialysis" as used herein refers to a primarily diffusive-type blood purification method wherein the differences in concentration drive the removal of uremic toxins and their passage through the dialyzer membrane which separates the blood from the dialysate. The expression "hemodiafiltration" as used herein refers to a blood purification method that combines diffusion and convection, wherein convection is achieved by applying a positive pressure gradient across the dialyzer membrane.

The hemodialyzers now accomplished are further characterized by clearance rates, determined according to ISO8637:2014(E), that in hemodialysis mode achieve values which can be achieved with prior art dialyzers only in hemodiafiltration mode, i.e. by applying a positive pressure gradient across the dialyzer membrane.

Dialyzers generally comprise a cylindrical housing or casing. Located within the interior of the casing is a fiber bundle. Typically the fiber bundle is comprised of a number of hollow fiber membranes that are oriented parallel to each other. The fiber bundle is encapsulated at each end of the dialyzer in a potting material to prevent blood flow around the fibers and to provide for a first flow space surrounding the membranes on the outside and a second flow space formed by the fiber cavities and the flow space above and below said potting material which is in flow communication with said fiber cavities. The dialyzers generally further consist of end caps capping the mouths of the tubular section of the device which also contains the fiber bundle.

The dialyzer body also includes a dialysate inlet and a dialysate outlet. According to one embodiment of the invention, the dialysate inlet and dialysate outlet define fluid flow channels that are in a radial direction, i.e., perpendicular to the fluid flow path of the blood. The dialysate inlet and dialysate outlet are designed to allow dialysate to flow into an interior of the dialyzer, bathing the exterior surfaces of the fibers and the fiber bundle, and then to leave the dialyzer through the outlet. The membranes are designed to allow blood to flow therethrough in one direction with dialysate flowing on the outside of the membranes in opposite direction. Waste products are removed from the blood through the membranes into the dialysate. Accordingly, dialyzers typically include a blood inlet and a blood outlet, the blood inlet being designed to cause blood to enter the fiber membranes and flow therethrough. Dialysate is designed to flow through an inlet of the dialyzer and out of the dialyzer through an outlet, thereby passing the outside or exterior walls of the hollow fiber membranes.

A variety of dialyzer designs can be utilized for accomplishing the present invention. According to one embodiment the hemodialyzers of the invention have designs such as those set forth in WO 2013/190022 A1. However, other designs can also be utilized without compromising the gist of the present invention.

The packing density of the hollow fiber membranes in the hemodialyzers of the present invention is from 50% to 65%, i.e., the sum of the cross-sectional area of all hollow fiber membranes present in the dialyzer amounts to 50 to 65% of the cross-sectional area of the part of the dialyzer housing comprising the bundle of semi-permeable hollow fiber membranes. According to one embodiment of the present invention, the packing density of the hollow fiber membranes in the hemodialyzers of the present invention is from 53% to 60%. If n hollow fiber membranes are present in the bundle of semi-permeable hollow fiber membranes, $D_F$ is the outer diameter of a single hollow fiber membrane, and $D_H$ is the inner diameter of the part of the dialyzer housing comprising the bundle, the packing density can be calculated according to $n*(D_F/D_H)^2$. A typical fiber bundle with fibers according to the invention, wherein the fibers have a wall thickness of 35 μm and an inner diameter of 180 μm, and which is located within a housing having an inner diameter of, for example, 38 mm, wherein the fibers have an effective fiber length of 236 mm and wherein packing densities of between 53% to 60% are realized, will contain about 12 500 to 13 500 fibers, providing for an effective surface area of about 1.7 $m^2$. In general, the effective surface area can be chosen to be in the ranges known in the art. Useful surface areas will lie, for example, in the range of from 1.1 $m^2$ to 2.5 $m^2$. It will be readily understood by a person skilled in the art that housing dimensions (inner diameter, effective length) will have to be adapted for achieving lower or higher membrane surface areas of a device, if fiber dimensions and packing densities remain the same.

According to one aspect of the present invention, a bundle of hollow fiber membranes is present in the housing or casing, wherein the bundle comprises crimped fibers. The bundle may contain only crimped fibers, such as described, for example, in EP 1 257 333 A1. According to another aspect of the invention, the fiber bundle may consist of 80% to 95% crimped fibers and from 5% to 15% non-crimped fibers, relative to the total number of fibers in the bundle, for instance, from 86 to 94% crimped fibers and from 6 to 14% non-crimped fibers. In one embodiment, the proportion of crimped fibers is from 86 to 92%. The fibers have a sinusoidal texture with a wavelength in the range of from 6 to 9 mm, for instance, 7 to 8 mm; and an amplitude in the range of from 0.1 to 0.5 mm; for instance 0.2 to 0.4 mm. Incorporation of 5 to 15% non-crimped fibers into a bundle of crimped semi-permeable hollow fiber membranes may enhance the performance of the hemodialyzer of the invention. For instance, with an unchanged packing density of the fibers within the dialyzer, the clearance of molecules like urea, vitamin B12, or cytochrome C from a fluid passing through the fiber lumen is increased. It is believed that this effect is due to improved flow of dialysis liquid in the second flow space of the dialyzer and around the individual fibers in the bundle. Another advantage of the incorporation of 5 to 15% non-crimped fibers into a bundle of crimped semi-permeable hollow fiber membranes is that packing densities can be achieved which are higher than those in bundles exclusively containing crimped fibers. As a consequence, a larger effective membrane area can be fitted into a given volume of the internal chamber of the hemodialyzer. Also, a given effective membrane area can be fitted into a smaller volume, which allows for further miniaturization of the hemodialyzer. Another alternative offered by the incorporation of 5 to 15% non-crimped fibers into a bundle of crimped semi-permeable hollow fiber membranes is that the crimp amplitude of the crimped fibers within the bundle can be increased at constant packing density and constant volume of the internal chamber, while the resilience of the bundle is kept at a value which does not require excessive force for the transfer of the bundle into the housing. This helps to avoid increased scrap rates in dialyzer production. When less than about 5%; of non-crimped fibers are present in the bundle of semi-permeable hollow fiber membranes, no substantial difference in dialyzer performance is observed in comparison to a dialyzer comprising crimped fibers only. On the other hand, when more than about 15% of non-crimped fibers are present in the bundle, a decrease of dialyzer performance is noted. A potential explanation for this effect could be that, with increasing proportion of non-crimped fibers within the bundle, non-crimped fibers may contact and adhere to each other, thus reducing membrane surface area available for mass transfer through the hollow fiber walls.

Figure 2:
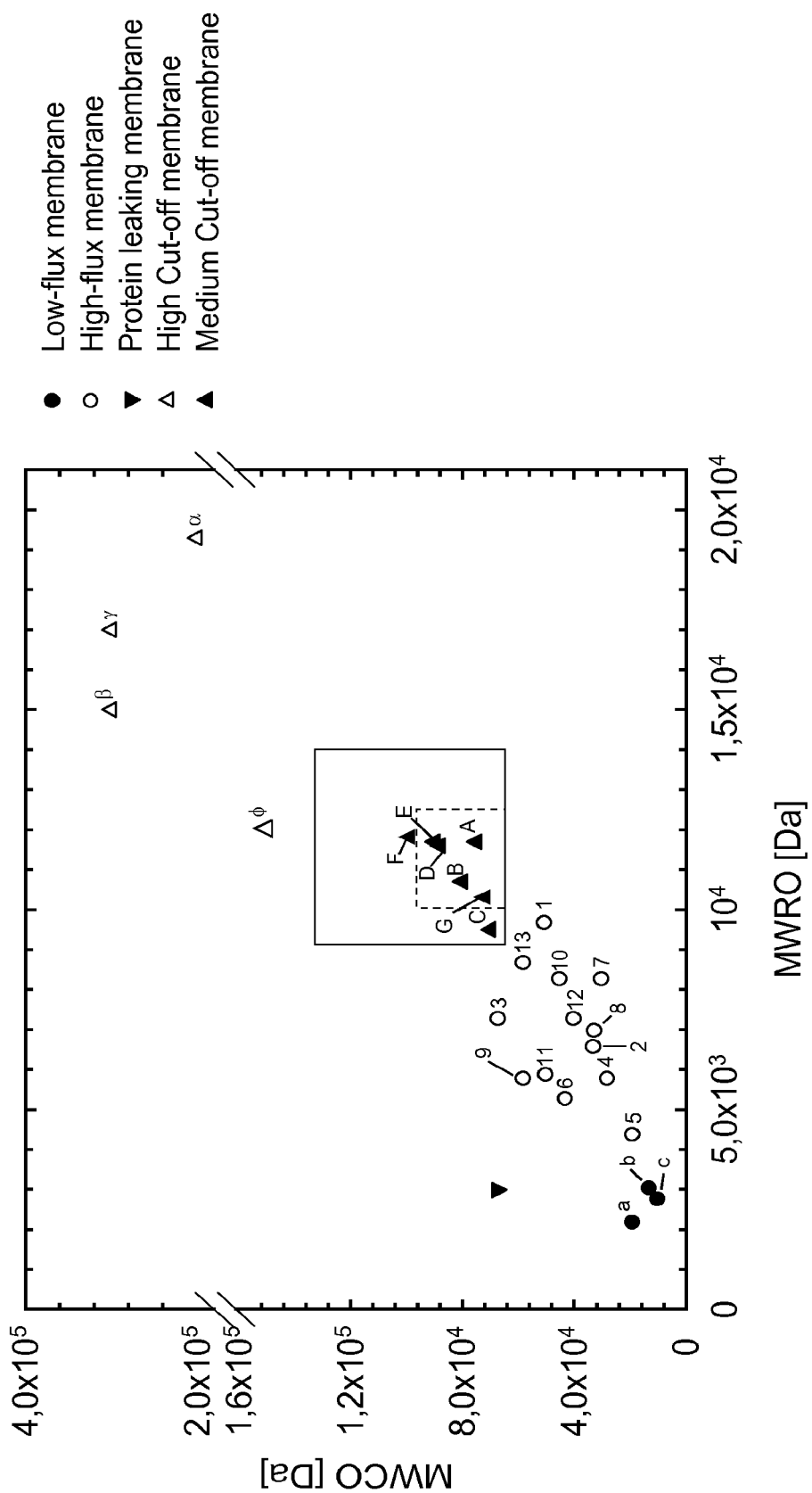
FIG. 2 shows the results of dextran sieving measurements wherein the MWRO (molecular weight retention onset) is plotted against the MWCO (molecular weight cut-off). Each measuring point represents three dextran sieving measurements of a given membrane. Dextran sieving measurements were performed according to Example 3. The respective MWCO and MWRO values were measured and the average value for a given membrane was entered into the graph shown. The membranes marked with a triangle (▲) and contained in two squares of varying sizes are membranes according to the invention and have been prepared in accordance with Example 1. The data points outside the square(s) are prior art membranes which are either low-flux membranes (●; a-c), high-flux membranes (○; 1-13), high cut-off membranes (Δ; α, β, γ, φ) or so-called protein-leaking membranes (▼). It is evident from the graph that the membranes according to the invention (▲; A-G) form a new type of membranes which in the representation of MWRO against MWCO is located between the high-flux and high cut-off membranes of the prior art. The respective membranes, the processes for preparing them and/or their identity are provided for in further detail in Example 1.

The hollow fiber membranes used for accomplishing the hemodialyzer of the present invention, due to their specific design, are characterized by an increased ability to remove larger molecules while at the same time effectively retaining albumin. The membranes are characterized by a molecular retention onset (MWRO) of between 9.0 kDa and 14.0 kDa and a molecular weight cut-off (MWCO) of between 55 kDa and 130 kDa as determined by dextran sieving (FIG. 2). Thus, according to one aspect of the present invention, the membranes are characterized by a MWRO of between 9000 and 14000 Daltons as determined by dextran sieving measurements, which indicates that the membranes according to the invention have the ability to let pass 90% of molecules having a molecular weight of from 9.0 to 14.5 kDa. Notably, said MWRO is achieved in hemodialysis (HD) mode. The molecules of said molecular weight range belong to the group of molecules generally referred to as middle molecules which otherwise can only efficiently be removed by certain high cut-off membranes at the cost of some albumin loss or by certain high-flux membranes which are used in HDF mode. According to another aspect of the invention, the membranes are further characterized by a MWCO of between 55 kDa and 130 kDa Daltons as determined by dextran sieving, which indicates that the membranes are able to effectively retain larger blood components such as albumin (67 kDa) and molecules larger than said albumin. In contrast, the average MWRO range of high-flux membranes lies in the range of from about 4 kDa to 10 kDa as determined by dextran sieving, combined with a MWCO of from about 19 kDa to about 65 kDa as determined by dextran sieving. High cut-off membranes are characterized by a significantly higher MWCO, as determined by dextran sieving, of from about 150-320 kDa, and a MWRO, as determined by dextran sieving of between 15-20 kDa.

According to another aspect of the present invention, the membranes of the invention have a MWRO, as determined by dextran sieving, in the range of from 9.0 kDa to 12.5 kDa and a MWCO, as determined by dextran sieving, in the range of from 55 kDa to 110 kDa. According to another aspect of the present invention, the membranes being part of the invention have a MWRO, as determined by dextran sieving, in the range of from 9.0 kDa to 12.5 kDa and a MWCO, as determined by dextran sieving, in the range of from 68 kDa to 110 kDa. According to yet another aspect of the present invention, the membranes have a MWRO, as determined by dextran sieving, in the range of from 10 kDa to 12.5 kDa and a MWCO, as determined by dextran sieving, in the range of from 68 kDa to 90 kDa. According to yet another aspect of the present invention, membranes have a MWRO, as determined by dextran sieving, of more than 10.0 kDa and less than 12.5 kDa and a MWCO, as determined by dextran sieving, of more than 65.0 kDa and less than 90.0 kDa.

As mentioned before, the membranes according to the invention are able to selectively control albumin loss and loss of other essential higher molecular weight blood components. In general, a hemodialyzer according to the invention with an effective membrane area of from 1.7 $m^2$ to 1.8 mA limits the protein loss in vitro ($Q_B$=300 ml/min, TMP=300 mmHg, bovine plasma with total protein concentration 60±5 g/l) after 25 minutes to a maximum of from 1.0 to 2.0 g/1. According to one embodiment of the invention the dialyzers with an effective membrane area of from 1.7 $m^2$ to 1.8 $m^2$ have a protein loss in vitro ($Q_B$=300 ml/min, TMP-300 mmHg, bovine plasma with total protein concentration 60±5 g/l) after 25 minutes of at most 1.2 or, according to another aspect of the invention, of at most 1.4 g/l. According to another aspect of the present invention, the hemodialyzer according to the invention with an effective membrane area of between 1.1 and 2.5 $m^2$ limits albumin loss per treatment (240 min±20%) at a blood flow of between 200-600 ml/min, a dialysate flow of between 300-1000 nil/min and an ultrafiltration rate of 0 to 30 ml/min, to a maximum of 7 g (Example 5). According to a further aspect of the invention the said effective surface area is between 1.4 and 2.2 $m^2$ and blow flow is between 200 and 500 ml/min, dialysate flow between 500 and 800 ml/min, and ultrafiltration rate between 0 and 20 ml/min. According to one aspect of the present invention, albumin loss under the aforementioned conditions is below 4 g. According to yet another aspect of the present invention, the above maximum values for albumin loss are reached at ultrafiltration rates of between 0 ml/min and 10 ml/min.

Membrane passage of a solute such as a protein which needs to be removed from blood or needs to be retained, as the case may be, is described by means of the sieving coefficient S. The sieving coefficient S is calculated according to $S=(2C_F)/(C_{Bin}+C_{Bout})$, where $C_F$ is the concentration of the solute in the filtrate and $C_{Bin}$ is the concentration of a solute at the blood inlet side of the device under test, and $C_{Bout}$ is the concentration of a solute at the blood outlet side of the device under test. A sieving coefficient of $S=1$ indicates unrestricted transport while there is no transport at all at $S=0$. For a given membrane each solute has its specific sieving coefficient. The membranes of the hemodialyzer according to the invention have an average sieving coefficient for albumin, measured in bovine plasma according to DIN EN ISO8637:2014 at $Q_B$=400 ml/min and UF=25 ml/min of between 0.01 and 0.2. According to another aspect of the invention, the membranes according to the invention have an average sieving coefficient for albumin, measured in bovine plasma according to DIN EN ISO8637:2014 at $Q_B$=400 ml/min and UF=25 ml/min of between 0.02 and 0.1. According to yet another aspect of the invention, the membranes according to the invention have an average sieving coefficient for albumin, measured in bovine plasma according to DIN EN ISO8637:2014 at $Q_B$=400 ml/min and UF=25 mil/min of between 0.02 and 0.08. According to another aspect of the invention, the membranes according to the invention have an average sieving coefficient for albumin, measured in bovine plasma according to EN1283 ($Q_B$max, UF=20%) at $Q_B$=600 ml/min and UF=120 ml/min of between 0.01 and 0.1. According to yet another aspect of the invention, the membranes according to the invention have an average sieving coefficient for albumin, measured in bovine plasma according to EN1283 ($Q_B$max, UF=20%) at $Q_B$=600 ml/min and UF=120 ml/min of between 0.01 and 0.06.

The semipermeable hemodialysis membrane of the hemodialyzer according to the invention comprises at least one hydrophilic polymer and at least one hydrophobic polymer. In one embodiment, said at least one hydrophilic polymer and at least one hydrophobic polymer are present as coexisting domains on the surface of the dialysis membrane. The hydrophobic polymer may be chosen from the group consisting of poly(aryl)ethersulfone (PAES), polysulfone (PSU) and polyethersulfone (PFS) or combinations thereof. In a specific embodiment of the invention, the hydrophobic polymer is chosen from the group consisting of poly (aryl) ethersulfone (PAES) and polysulfone (PSU). The hydrophilic polymer will be chosen from the group consisting of polyvinylpyrrolidone (PVP), polyethyleneglycol (PEG), polyvinylalcohol (PVA), and a copolymer of polypropyleneoxide and polyethyleneoxide (PPO-PEO). In another embodiment of the invention, the hydrophilic polymer may be chosen from the group consisting of polyvinylpyrrolidone (PVP), polyethyleneglycol (PEG) and polyvinylalcohol (PVA). In one specific embodiment of the invention, the hydrophilic polymer is polyvinylpyrrolidone (PVP).

The membrane used for accomplishing the hemodialyzer of the invention is a hollow fiber having an asymmetric foam- or sponge-like and/or a finger-like structure with a separation layer present in the innermost layer of the hollow fiber. According to one embodiment of the invention, the hollow fiber membrane used has an asymmetric "sponge-like" or foam structure (FIG. 9). According to another embodiment of the invention, the membrane of the invention has an asymmetric structure, wherein the separation layer has a thickness of less than about 0.5 μm. In one embodiment, the separation layer contains pore channels having an average pore size (radius) of between about 5.0 and 7.0 nm as determined from the MWCO based on dextran sieving coefficients according to Boschetti-de-Fierro et al. (2013) and Granath et al. (1967). The average pore size (radius) before blood contact is generally above 5.0 nm and below 7.0 nm for this type of membrane (FIG. 8) and specifically above 5.0 nm and below 6.7 nm. The next layer in the hollow fiber membrane is the second layer, having the form of a sponge structure and serving as a support for said first layer. In a preferred embodiment, the second layer has a thickness of about 1 to 15 μm. The third layer has the form of a finger structure. Like a framework, it provides mechanical stability on the one hand; on the other hand a very low resistance to the transport of molecules through the membrane, due to the high volume of voids, is achieved. The third layer has a thickness of 20 to 30 μm. In another embodiment of the invention, the membranes can be described to include a fourth layer, which is the outer surface of the hollow fiber membrane. This fourth layer has a thickness of about 1 to 10 μm. As can easily be understood, a combination of the above ranges will always add up to a wall thickness within the aforementioned ranges for wall thicknesses of the hollow fiber membranes in accordance with the present invention.

The manufacturing of a membrane as it is used for accomplishing the present invention follows a phase inversion process, wherein a polymer or a mixture of polymers is dissolved in a solvent or solvent mixture to form a polymer solution. The solution is degassed and filtered before spinning. The temperature of the polymer solution is adjusted during passage of the spinning nozzle (or slit nozzle) whose temperature can be regulated and is closely monitored. The polymer solution is extruded through said spinning nozzle (for hollow fibers) or a slit nozzle (for a flat film) and after passage through the so-called spinning shaft enters into said precipitation bath containing a non-solvent for the polymer and optionally also a solvent in a concentration of up to 20 wt.-%. To prepare a hollow fiber membrane, the polymer solution preferably is extruded through an outer ring slit of a nozzle having two concentric openings. Simultaneously, a center fluid is extruded through an inner opening of the spinning nozzle. At the outlet of the spinning nozzle, the center fluid comes into contact with the polymer solution and at this time the precipitation is initialized. The precipitation process is an exchange of the solvent from the polymer solution with the non-solvent of the center fluid. By means of this exchange the polymer solution inverses its phase from the fluid into a solid phase. In the solid phase the pore structure and the pore size distribution is generated by the kinetics of the solvent/non-solvent exchange. The process works at a certain temperature which influences the viscosity of the polymer solution. For preparing membranes according to the invention, the temperature of the spinning nozzle and, consequently, of the polymer solution and the center fluid as well as the temperature of the spinning shaft should be carefully controlled. In principle, membranes of the invention can be prepared at a comparatively broad temperature range. Temperature may thus be in the range of between 30 and 70° C. However, for producing a membrane of the invention, the ultimate temperature should be chosen by taking account of the polymer composition and the temperature which would otherwise be used for producing a standard high-flux membrane with about the same polymer composition and which can be used as a starting point for the production of a membrane according to the invention. In general, there are two parameters which can be effectively influenced in order to arrive at membranes of the present invention. First, the temperature at the spinning nozzle should be slightly raised by about 0.5° C. to 4° C. relative to the temperatures used for producing a high-flux type membrane having about the same polymer composition, resulting in a corresponding increase of the temperature of the polymer solution. Second, the water content in the center solution should be slightly reduced in a range of from 0.5 wt.-% to 4 wt.-%, preferably from 0.5 wt.-% to 3 wt.-%. It should be obvious that the polymer composition for preparing a membrane according to the invention does not have to be completely identical to a typical polymer composition for preparing a high-flux membrane, such as, for example, Membrane 6 (Example 1). Accordingly, expressions such as "about the same polymer composition" as used in the present context refers to polymer compositions having the same basic composition, for example, a combination of PS, PES or PAES on the one hand and PVP on the other hand, in concentrations typically used for the production of high-flux type membranes and/or membranes according to the present invention.

As mentioned before, the temperature influences the viscosity of the spinning solution, thereby determining the kinetics of the pore-forming process through the exchange of solvent with non-solvent. The viscosity of a spinning solution for preparing membranes according to the invention generally should be in the range of from 3000 to 7400 mPas at 22° C. According to one embodiment of the invention, the viscosity is in the range of from 4900 to 7400 mPas (22° C.). According to yet another embodiment of the invention the viscosity will be in the range of from 4400 to 6900 mPas (22° C.). For arriving at foam- or sponge-like structures the viscosity can, for example, be increased to values of up to 15000 mPas, even though such structures can also be obtained with lower values in the above-stated ranges.

Another aspect of preparing a membrane comprised by the hemodialyzer according to the invention concerns the temperature of the center fluid. The center fluid generally comprises 45 to 60 wt.-% of a precipitation medium, chosen from water, glycerol and other alcohols, and 40 to 55 wt.-% of solvent. In other words, the center fluid does not comprise any hydrophilic polymer. The temperature of the center fluid is in principle the same as the temperature chosen for the spinning nozzle as the temperature of the center fluid will be determined when it passes through said nozzle. According to one embodiment of the invention, the center fluid is composed of water and NMP, wherein the water is present in a concentration of from 50 to 58 wt.-%.

According to a further embodiment of the invention, the polymer solution coming out through the outer slit openings is, on the outside of the precipitating fiber, exposed to a humid steam/air mixture. Preferably, the humid steam/air mixture in the spinning shaft has a temperature of between 50° C. to 60° C. According to one embodiment of the invention, the temperature in the spinning shaft is in the range of from 53° C. to 58° C. The distance between the slit openings and the precipitation bath may be varied, but generally should lie in a range of from 500 mm to 1200 mm, in most cases between 900 mm and 1200 mm. According to one embodiment of the invention the relative humidity is >99%.

According to another aspect of the present invention, following passage through the spinning shaft the hollow fibers enter a precipitation bath which generally consists of water having a temperature of from 12° C. to 30° C. For preparing the membranes according to the invention, the temperature of the precipitation bath may be slightly elevated by 1 to 10° C. in comparison to the temperature which would otherwise be chosen for preparing a high-flux or high cut-off membrane. According to one embodiment of the invention an increase by 2° C. to 10° C. and more specifically an increase of up to 6° C. may be recommendable to arrive at membranes of the present invention.

According to one specific embodiment of the invention, the temperature of the precipitation bath is between 23° C. and 28° C. The membrane according to the present invention will then be washed in consecutive water baths to remove waste components and can then directly be submitted to, for example, online drying at temperatures of between 150° C. to 280° C. without any further treatment such as the below mentioned salt bath.

In order to illustrate what has been said before, a membrane according to the invention can be produced as follows. For a composition based on poly(aryl)ethersulfone, polyethersulfone or polysulfone and PVP, the temperature of the spinning nozzle, for example, can be chosen to be in a range of from 56° C. to 59° C., and the temperature of the spinning shaft is then in the range of from 53° C. to 56° C. in order to reliably arrive at a membrane according to the invention. Preferably, the temperature of the spinning nozzle is in the range of from 57° C. to 59° C., more preferably in a range of from 57° C. to 58° C., and the temperature in the spinning shaft is then in the range of from 54° C. to 56° C. In each case the viscosity of the spinning solution after preparation should be in the range of from 3000 to 7400 mPas at 22° C. Such composition, may, for example, comprise 14 wt.-% of poly(aryl)ethersulfone, polyethersulfone or polysulfone, 7 wt.-% of PVP, 77 wt.-% of a solvent, such as NMP, and 2 wt.-% of water. At the same time, the center solution should comprise, for example, 54.0 to 55 wt.-% water and 46.0 to 45.0 wt.-% solvent, e.g. NMP, respectively. For example, the center solution may contain 54.5% water and 45.5 solvent, such as NMP.

The spinning velocity often may influence the properties of the resulting membranes. In the present case, the velocity may be chosen to be in a relatively broad range from about 10 to 60 m/min without departing from the invention, even though higher spinning velocities which still provide for a stable production process will be desirable for economic reasons. According to one embodiment of the invention, the spinning velocity for arriving at membranes as used for accomplishing hemodialyzers according to the invention will therefore be in the range of from 30 to 50 m/min. According to another embodiment of the invention, the spinning velocity for arriving at membranes as used for accomplishing hemodialyzers according to the invention will be in the range of from 40 to 55 m/min.

According to one embodiment of the invention, the polymer solution used for preparing the membrane preferably comprises 10 to 20 wt.-% of the hydrophobic polymer, 2 to 11 wt.-% of the hydrophilic polymer, as well as water and a solvent, such as, for example, NMP. Optionally, low amounts of a second hydrophobic polymer can be added to the polymer solution. The spinning solution for preparing a membrane according to the present invention preferably comprises between 12 and 15 weight-h of polyethersulfone or polysulfone as hydrophobic polymer and 5 to 10 weight-% of PVP, wherein said PVP may consist of a low and a high molecular PVP component. The total PVP contained in the spinning solution thus may consist of between 22 and 34 weight-% and preferably of between 25 and 30 weight-% of a high molecular weight component and of between 66 and 78 weight-%, preferably of between 70 and 75 weight-% of a low molecular weight component. Examples for high and low molecular weight PVP are, for example, PVP K85/K90 and PVP K30, respectively. The solvent may be chosen from the group comprising N-methylpyrrolidone (NMP), dimethyl acetamide (DMAC), dimethyl sulfoxide (DMSO) dimethyl formamide (DMF), butyrolactone and mixtures of said solvents. According to one embodiment of the invention, the solvent is NMP.

As mentioned before, the type, amount and ratio of hydrophilic and hydrophobic polymers used for producing membranes according to the invention may be similar to or the same as those which would otherwise be used for the production of high-flux membranes which are known in the art. It may, however, be recommendable for arriving at membranes according to the invention to adjust the ratio of water and solvent (H$_2$O/solvent) in the polymer solution compared to standard high-flux recipes to slightly lower values, i.e. to slightly decrease the total concentration of water in the polymer solution by about 0.5 wt.-% to 4 wt.-% and to adjust the amount of solvent accordingly by slightly increasing the total concentration of the respective solvent.

In other words, for a given polymer solution, the amount of water will be slightly reduced and the amount of solvent will at the same time and rate be slightly increased compared to polymer compositions used for standard high-flux membranes As an alternative way to arrive at membranes for hemodialyzers according to the invention it is also possible to choose, as a starting point, known recipes and processes for preparing high cut-off membranes. In this case, the polymer composition, including water and solvent, will generally remain about the same as a composition typically used for preparing high cut-off membranes, such as shown for Membranes α and β. However, the ratio of $H_2O$ and solvent in the center solution should be increased as compared to the typical center solution used for preparing a high cut-off membrane, such as, for example, for Membranes α and β, i.e. the water content is slightly increased by about 0.5 wt.-% to 4.0 wt.-%.

The slight increase in the water content in the center solution should be accompanied by an adaption of the spinning nozzle and spinning shaft temperature. An increase in water content will generally be accompanied by appropriately adapting the temperature of the spinneret and the spinning shaft by up to 4° C., preferably by about between 0.5° C. to 3° C., relative to the respective temperatures used for producing a high cut-off type membrane. Depending on the aspired characteristics of the membranes according to the invention in terms of MWRO and MWCO values, the change in the water content of the center solution can be accompanied, for example, by a temperature increase of up to 4° C., preferably by 0.5° C. to 3° C., resulting in rather open-pored membrane species which would be located in the upper right corner of the square shown in FIG. 2. It may also be accompanied by a very slight or no significant increase of the temperature or even by a decrease of the spinneret's and spinning shaft's temperature by about 0.5° C. to 2° C., respectively, resulting in a less open-pored, more high-flux like membrane species which would be located in the lower left corner of the square shown in FIG. 2.

Accordingly, it is one aspect of the present invention, that the membranes according to the invention can be obtained by dissolving at least one hydrophobic polymer component and at least one hydrophilic polymer in at least one solvent to form a polymer solution having a viscosity of from 3000 to 7400 mPas at a temperature of 22° C., extruding said polymer solution through an outer ring slit of a spinning nozzle with two concentric openings and extruding a center fluid comprising at least one solvent and water through the inner opening of the nozzle, passing the polymer solution through a spinning shaft into a precipitation bath, wherein the distance between the slit openings and the precipitation bath is between 500 mm to 1200 mm, preferably between 900 mm and 1200 mm, and wherein the relative humidity of the steam/air mixture in the spinning shaft is between 60% and 100%, washing the membrane obtained, drying said membrane and, optionally, sterilizing said membrane by steam treatment, wherein the content of water in the center solution is increased by between 0.5 wt.-% and 4 wt.-% relative to the water content which is used for preparing a high-cut off membrane having the same polymer composition, and wherein the temperature of the spinning nozzle and the spinning shaft is either decreased by up to 2.0° C., preferably by 0.5° C. to 2° C., relative to the temperature which would be used for preparing a high-cut off membrane having the same polymer composition, or is increased by 0.5° C. to 4° C., preferably 0.5° C. to 3° C., relative to the temperature which would be used for preparing a high-cut off membrane having the same polymer composition, or remains the same.

The membrane after washing and without being immersed in any salt bath can directly be submitted to a drying step, such as online drying, and is then preferably steam sterilized at temperatures above 121° C. for at least 21 minutes. It is, however, also possible to use other methods known in the art for sterilizing the membrane and/or the filter device comprising same.

A membrane according to the invention which is based on, for example, poly(aryl)ethersulfone and PVP, after preparation comprises from between 2.0 wt.-% to 4.0 wt.-% PVP and poly(aryl)ethersulfone adding up to 100%, respectively.

Hollow fiber membranes as used in hemodialyzers according to the invention can be produced with different inner and outer diameters and the wall thickness of such hollow fiber membranes may vary over a certain range. High cut-off membranes known in the art, such as, for example, Theralite® and HCO1100®, have a comparatively large inner diameter of the fiber of 215 µm and a wall thickness of 50 µm. Known high-flux membranes such as used, for example, in the Revaclear®400 filter have inner diameters of 190 µm and a wall thickness of 35 µm, or, in the case of the FX CorDiax hemodiafilters, an inner diameter of 210 µm. Membranes according to the invention are preferably prepared with a wall thickness of below 55 µm, generally with a wall thickness of from 30 to 49 µm. The membranes can, however, be produced with a wall thickness of below 40 µm, generally in the range of about 30 to 40 µm, such as, for example, with a wall thickness of 35 µm. The inner diameter of the hollow fiber membranes of the present invention may be in the range of from 170 µm to 200 µm, but may generally be reduced to below 200 µm or even below 190 µm, for example to about 175 µm to 185 µm for full efficiency in the context of the present invention.

The membranes used in hemodialyzers according to the invention can be further characterized by an average sieving coefficient for β2-M, measured in bovine plasma (total protein 60±5 g/l total protein) according to EN1283 ($Q_B$max, UF=20%) with blood flow rates of between 400 ml/min and 600 ml/min of between 0.7 and 1. According to another embodiment of the invention the sieving coefficients for β2-M under the same conditions are between 0.8 and 1. According to yet another embodiment of the invention the sieving coefficients for β2-M under the same conditions are between 0.9 and 1. According to another embodiment of the invention the sieving coefficients for β2-M measured according to DIN EN ISO8637:2014 at $Q_B$–400 ml/min and UF-25 ml/min are between 0.8 and 1. According to yet another embodiment of the invention the sieving coefficients for β2-M under the same conditions are between 0.9 and 1.

The membranes can also be characterized by an average sieving coefficient for myoglobin, measured in bovine plasma according to EN1283 ($Q_B$max, UF=20%) with blood flow rates of between 400 ml/min and 600 ml/min of between 0.7 and 1. According to another embodiment of the invention the sieving coefficients for myoglobin under the same conditions are between 0.8 and 1, more specifically between 0.9 and 1. According to another embodiment of the invention the sieving coefficients for myoglobin, measured according to DIN EN ISO8637:2014 at $Q_B$–400 ml/min and UF-25 ml/min are between 0.8 and 1. According to yet another embodiment of the invention the sieving coefficients for myoglobin under the same conditions are between 0.9 and 1.

The blood flow rates which can be used with devices comprising the membranes according to the invention are in the range of from 200 ml/min to 600 ml/min. Dialysate flow rates for use with the membranes according to the invention are in the range of from 300 ml/min to 1000 ml/min. Usually, blood flow rates of from 300 ml/min to 500 ml/min, dialysis flow rates of from 500 ml/min to 800 ml/min and UF rates of from 0 to 15 ml/min will be used. For example, a standard flow rate used is $Q_B$=300 ml/min, $Q_D$=500 ml/min and UF=0 ml/min.

Due to the combination of the housing design, the physical properties of the single fibers and of the fiber bundle with the new type of membranes according to the invention, the hemodialyzers of the invention are especially beneficial for the treatment of chronic and acute renal failure by hemodialysis, thereby achieving and even exceeding a performance which can currently be achieved only in hemodiafiltration therapy. The new combined features allow the highly efficient removal of uremic molecules ranging from small to large molecular weight (FIG. 1) while efficiently retaining albumin and larger essential proteins. State of the art membranes at the most achieve a similar performance in HDF treatment modes.

This becomes especially apparent when considering the clearance performance of the hemodialyzers of the invention. The clearance C (ml/min) refers to the volume of a solution from which a solute is completely removed per time unit. In contrast to the sieving coefficient which is the best way to describe the structure and performance of a membrane as the essential component of a hemodialyzer, clearance is a measure of the overall dialyzer design and function and hence dialysis effectiveness. The clearance performance of a dialyzer can be determined according to DIN EN ISO8637:2014. Clearance therefore is used herein to describe the excellent performance which can be achieved by using the aforementioned highly efficient membranes in a hemodialyzer as described above.

With a hemodialyzer according to the invention excellent clearance rates as determined in vitro according to Example 4 with, for example, a $Q_B$ between 200 ml/min and 500 ml/min, a $Q_D$ of 500 ml/min and an UF of 0 ml/min and an effective surface area of from 1.6 m² to 1.8 m² for molecules covering a broad range of uremic toxins of various molecular weights (see Table IV) can be achieved. Ultrafiltration rates may be increased to about 20 ml/min or to 30 ml/min without departing from the invention. Generally, ultrafiltration rates will be in the range of from 0 to 20 ml/min or 0 to 15 ml/min, but can also be chosen to be 0 to 10 ml/min or simply 0 ml/min. In general, clearance rates determined in vitro according to DIN EN ISO8637:2014 at a $Q_B$ between 200 ml/min and 500 ml/min, a $Q_D$ of 500 ml/min and an UF of 0 ml/min and an effective surface area of 1.7 m² to 1.8 m² for small molecular weight substances such as, for example, urea, are in the range of between 190 and 400 ml/min can be achieved; such rates are superior, but at least equivalent to the current state of the art hemodialysis filters. The same is true for clearance rates for other small molecules such as creatinine and phosphate, which are in the range of between 190 and 380 ml/min. Thus, the hemodialyzers according to the invention can achieve better clearance rates for higher molecular weight blood components without a drop in clearance performance for small molecules, which is often the case with hemodialyzers which have been described before. Clearance rates as determined according to DIN EN ISO8637:2014 at a $Q_B$ between 200 ml/min and 500 ml/min, a $Q_D$ of 500 ml/min and an UF of 0 ml/min for vitamin $B_{12}$, for example, are in the range of from 170 to 280 ml/min, for inulin clearance rates of between 140 and 240 ml/min can be achieved, respectively. Clearance rates for myoglobin are in the range of between 110 and 200 ml/min. Clearance rates for cytochrome C as determined according to DIN EN ISO8637:2014 at a $Q_B$ between 200 ml/min and 500 ml/min, a $Q_D$ of 500 ml/min and an UF of 0 ml/min (Tables VI through VIII) are in the range of between 130 and 200 ml/min. For example, cytochrome C clearance values of the hemodialyzer of the invention as determined according to DIN EN ISO8637: 2014 at a $Q_B$ between 200 ml/min and 500 ml/min, a $Q_D$ of 500 ml/min and an UF of 0 ml/min are significantly higher than the corresponding values of state of the art dialyzers used in hemodialysis therapy (see Table VI), and are even superior, under hemodialysis conditions, to the clearance performance of current state of the art hemodiafilters determined under HDF condition with increased ultrafiltration rates (Table VII). The hemodialyzers according to the invention under hemodialysis conditions (for example, UF=0 ml/min) achieve values which are comparable to what can be achieved with state of the art hemodiafilters measured at high ultrafiltration rates (Table VIII).

It will be readily apparent to one skilled in the art that various substitutions and modifications may be made to the invention disclosed herein without departing from the scope and spirit of the invention.

The present invention will now be illustrated by way of non-limiting examples in order to further facilitate the understanding of the invention.

EXAMPLES

Example 1

Preparation of Membranes 1.1 Membrane A

Two solutions were used for the formation of the membrane, the polymer solution consisting of hydrophobic and hydrophilic polymer components dissolved in N-methyl-pyrrolidone, and the center solution being a mixture of N-methyl-pyrrolidone (NMP) and water. The polymer solution contained poly(aryl)ethersulfone (PAES 14.0 wt-%) and polyvinylpyrrolidone (2 wt-% of PVP K85 and 5 wt-% of PVP K30, a total PVP concentration in the polymer solution of 7 wt %). The solution further contained NMP (77.0 wt-%) and water (2.0 wt-%). The viscosity of the polymer solution, measured at a temperature of 22° C., was between 5500 and 5700 mPas. The spinneret was heated to a temperature of 59° C. The center solution contained water (54.5 wt-%) and NMP (45.5 wt-%). A defined and constant temperature regime was applied to support the process. The center solution was pre-heated to 59° C. and pumped towards the two-component hollow fiber spinneret. The polymer solution was leaving the spinneret through an annular slit with an outer diameter of 500 mm and an inner diameter of 350 mm/center solution slit 180 mm. The center fluid was leaving the spinneret in the center of the annular polymer solution tube in order to start the precipitation of the polymer solution from the inside and to determine the inner diameter of the hollow fiber. The two components (polymer solution and center fluid) were entering a space separated from the room atmosphere at the same time. This space is referred to as spinning shaft. A mixture of steam (~100° C.) and air (22° C.) was injected into the spinning shaft. The temperature in the spinning shaft was adjusted by the ratio of steam and air to 56° C. The length of the spinning shaft was 1050 mm. By the aid of gravity and a motor-driven roller, the hollow fiber was drawn from top to bottom, from spinneret through the spinning shaft into a water bath. The water bath had a temperature of 25° C. The spinning velocity was about 45 m/min. The hollow fiber was subsequently led through a cascade of water baths with temperatures increasing from 25° C. to 76° C. The wet hollow fiber membrane leaving the water-rinsing bath was dried in a consecutive online drying step. The hollow fiber was collected on a spinning wheel in the shape of a bundle. In some batches an additional texturizing step was added before the bundle was prepared.

Alternatively, hand bundles according to Example 2 were formed for further experiments (see also Examples 3 and 4). Scanning micrographs of the outer surface and of the hollow fiber according to Example 1.1 are shown in FIG. 8. The membrane has a finger-like structure. The inner diameter of Membrane A was adjusted to be 180 μm and the wall thickness was chosen to be 35 μm.

1.2 Membrane B

Membrane B is based on the same polymer solution and center solution as Membrane A of Example 1.1 and was produced in analogy to what is described there. Differences were introduced only with regard to the temperature of the spinneret, which was adjusted to 58° C., the temperature of the spinning shaft, which was adjusted to 55° C. The temperature of the center solution was adjusted to 58° C. via the spinning nozzle.

1.3 Membrane C

Membrane C is based on the same polymer solution and center solution as Membrane A of Example 1.1 and was produced in analogy to what is described there. Differences were introduced only with regard to the temperature of the spinneret, which was adjusted to 57° C., and the temperature of the spinning shaft, which was adjusted to 54° C. The temperature of the center solution was adjusted to 57° C. via the spinning nozzle.

1.4 Membrane D

Membrane D is based on the same polymer solution and center solution as in Example 1.1 and was produced in analogy to what is described there. Differences were introduced only with regard to the polymer viscosity which in this case was 5071 mPas. The temperature of the center fluid was according to the spinning nozzle.

1.7 Membrane E

Membrane E is based on the same polymer solution and center solution as described in Example 1.1 and was produced in analogy to what is described there. In this case, the sieving data obtained slightly varied from data obtained with membranes prepared according to Example 1.1.

1.6 Membrane F

For obtaining sponge-like membrane structures, the polymer solution in contrast to Examples 1.1 to 1.5 contained a slightly different composition but was otherwise produced in analogy to what is described in Example 1.1. The solution contained poly(aryl)ethersulfone (PAES 14.0 wt-%) and polyvinylpyrrolidone (2 wt-% of PVP K85 and 5 wt-% of PVP K30). The solution further contained NMP (73.0 wt-%) and water (6.0 wt-%). The spinneret was heated to a temperature of 57° C. The center solution contained water (49.0 wt-%) and NMP (51.0 wt-%). The center solution was kept at 57° C. The temperature in the spinning shaft was adjusted to 55° C. The length of the spinning shaft was 1000 mm. The spinning velocity was 45 m/min. Scanning micrographs of the outer surface and of the hollow fiber according to Example 1.6 are shown in FIG. 9. The inner diameter of Membrane F was again adjusted to be 180 μm and the wall thickness was again chosen to be 35 μm.

1.7 Membrane G

Membrane G was based on the same polymer solution as described in Example 1.6 (Membrane F) and was produced in analogy to what is described there. Differences were introduced with regard to the temperature of the spinneret, which was adjusted to 58° C., and the temperature of the spinning shaft, which was adjusted to 56° C. The temperature of the center solution was adjusted to 58° C. via the spinning nozzle. The inner diameter of Membrane G was again adjusted to be 180 μm and the wall thickness was again chosen to be 35 μm.

1.8 Comparative Example: High Cut-Off Membrane β

The polymer solution used for preparing a high cut-off Membrane β (see FIG. 2) according to the prior art was identical to the polymer solution used for the preparation of Membrane A (Example 1.1). However, the center solution used contained 53.0 wt.-% water and 47.0 wt.-% NMP. During the membrane formation process polymer and center solution were brought in contact with a spinneret and the membrane precipitated. The spinning velocity was 45 m/min. A defined and constant temperature regime was applied to support the process, wherein the spinneret was kept at a temperature of 58° C. The precipitated hollow fiber fell through a spinning shaft having a height of 1050 mm which was filled with steam (>99% relative humidity). The temperature within the shaft was stabilized to 54° C. Finally, the fiber entered a washing bath containing about 4 wt-% NMP in water, wherein the bath was kept a temperature of 20° C. The membrane was further washed in two additional water baths (75° C. and 65° C.) with counter current flow (250 l/h). Membrane drying was performed online, wherein remaining water was removed. The fibers had an inner diameter of 215 μm and a wall thickness of 50 μm.

1.9 Comparative Example: High Cut-Off Membrane α

The polymer solution and center solution as well as the process used for preparing the high cut-off Membrane α according to the prior art was identical to the polymer solution used for the preparation of Membrane β (Example 1.8). Differences existed with regard to the spinning velocity, which was lower than in Example 1.8 (29 m/min) and the online drying step, which in this case was omitted.

1.10 Comparative Example: High Cut-Off Membrane γ

The polymer solution and center solution as well as the process used for preparing the high cut-off Membrane γ according to the prior art was identical to the polymer solution used for the preparation of Membrane β (Example 1.8). Differences were introduced with regard to spinning velocity (34 m/min) and with regard to the temperature of the spinning shaft (56° C.).

1.11 Comparative Example: High Cut-Off Membrane φ

Membrane #(FIG. 2) refers to hollow fiber membranes which were extracted from a Phylther® hemodialyzer (Phylther® HF 22 SD (2.2 m², Bellco, Italy)). The hollow fiber membranes are based on polyphenylene. The hollow fibers were used for preparing standardized mini-modules according to Example 2 for further tests.

1.12 Comparative Example: High-Flux Membrane 1

Membrane 1 (FIG. 2) refers to hollow fiber membranes which were extracted from a PES-21 Dα$^{eco}$ hemodialyzer (Nipro, Japan). The hollow fiber membranes are polyethersulfone based membranes (Polynephron®). The hollow fibers were used for preparing standardized mini-modules according to Example 2 for further tests.

1.13 Comparative Example: High-Flux Membrane 2

Membrane 2 (FIG. 2) refers to hollow fiber membranes which were extracted from an APS 21EA hemodialyzer (2.1 m², Asahi Kasei Medical Co., Ltd.). The hollow fiber membranes are polysulfone based membranes with a wall thickness of 45 μm and an inner diameter of 180 μm. The hollow fibers were used for preparing standardized mini-modules according to Example 2 for further tests.

1.14 Comparative Example: High-Flux Membrane 3

Membrane 3 (FIG. 2) refers to hollow fiber membranes which were extracted from a Phylther® HF 17 G (1.7 m², Bellco, Italy)). The hollow fiber membranes are based on polyphenylene. The hollow fibers were used for preparing standardized mini-modules according to Example 2 for further tests.

1.15 Comparative Example: High-Flux Membrane 4

Membrane 4 (FIG. 2) refers to hollow fiber membranes which were extracted from a FX-S 220 filter (2.2 m², Fresenius Medical Care Japan KK) which is based on polysulfone and has a wall thickness of 35 μm and an inner diameter of 185 μm. The hollow fibers were used for preparing standardized mini-modules according to Example 2 for further tests.

1.16 Comparative Example: High-Flux Membrane 5

Membrane 5 (FIG. 2) refers to hollow fiber membranes which were extracted from an Optiflux® F180NR filter (1.8 m², Fresenius Medical Care North America) which is based on polysulfone and has a wall thickness of 40 μm and an inner diameter of 200 μm. The hollow fibers were used for preparing standardized mini-modules according to Example 3 for further tests.

1.17 Comparative Example: High-Flux Membrane 6

Membrane 6 (FIG. 2) refers to hollow fiber membranes which were prepared in accordance with Example 1 of EP 2 113 298 A1. The temperatures of the spinneret and the spinning shaft were chosen to be 56° C. and 53° C., respectively, and the height of the spinning shaft was adjusted to the same heights as chosen in Example 1.1. The temperature of the water bath was adjusted to 20° C. The hollow fibers were assembled in standardized mini-modules according to Example 2 for further tests.

1.18 Comparative Example: High-Flux Membrane 7

Membrane 7 (FIG. 2) refers to hollow fiber membranes which were extracted from an FDY-210GW filter (2.1 m² from Nikkiso Co., LTD.) which comprises a so-called PEPA® membrane (Polyester-Polymer Alloy, with PVP) having a wall thickness of 30 μm and an inner diameter of 210 μm. The dialyzer was developed for applications that require an extended sieving coefficient profile. The hollow fibers were used for preparing standardized mini-modules according to Example 2 for further tests.

1.19 Comparative Example: High-Flux Membrane 8

Membrane 8 (FIG. 2) refers to hollow fiber membranes which were extracted from an FDY-21GW filter (2.1 m² from Nikkiso Co., LTD.) which comprises a so-called PEPA® membrane (Polyester-Polymer Alloy) having a wall thickness of 30 μm and an inner diameter of 210 μm. The hollow fibers were used for preparing standardized mini-modules according to Example 2 for further tests.

1.20 Comparative Example: High-Flux Membrane 9

Membrane 9 (FIG. 2) refers to hollow fiber membranes which were extracted from an FLX-21 GW filter (2.1 m² from Nikkiso Co., LTD., PVP-free) which comprises a so-called PEPA® membrane (Polyester-Polymer Alloy) having a wall thickness of 30 μm and an inner diameter of 210 μm. The hollow fibers were used for preparing standardized mini-modules according to Example 2 for further tests.

1.21 Comparative Example: High-Flux Membrane 10

Membrane 10 (FIG. 2) refers to hollow fiber membranes which were extracted from a PES-21 SEα$^{eco}$ hemodialyzer (Nipro, Japan). The hollow fiber membranes are polyethersulfone based membranes. The hollow fibers were used for preparing standardized mini-modules according to Example 2 for further tests.

1.22 Comparative Example: High-Flux Membrane 11

Membrane 11 (FIG. 2) refers to hollow fiber membranes as used in Polyflux® 170H filters (1.7 m², Gambro Lundia AR) which are based on a blend of polyarylethersulfone (PAES), polyvinylpyrrolidone (PVP) and polyamide and have a wall thickness of 50 μm and an inner diameter of 215 μm. The hollow fibers were assembled in standardized mini-modules according to Example 2 for further tests.

1.23 Comparative Example: High-Flux Membrane 12

Membrane 12 (FIG. 2) refers to hollow fiber membranes which were extracted from an EMiC®2 filter (1.8 m² from Fresenius Medical Care Deutschland GmbH). The respective hollow fibers are based on polysulfone and have a wall thickness of 35 µm and an inner diameter of 220 µm. The hollow fibers were used for preparing standardized mini-modules according to Example 2 for further tests.

1.24 Comparative Example: High-Flux Membrane 13

Membrane 13 (FIG. 2) refers to hollow fiber membranes which were extracted from a PES-21 Sα$^{eco}$ hemodialyzer (Nipro, Japan). The hollow fiber membranes are polyethersulfone based membranes. The hollow fibers were used for preparing standardized mini-modules according to Example 2 for further tests.

1.25 Comparative Example: Low-Flux Membrane α

Membrane a (FIG. 2) refers to hollow fiber membranes as used in Polyflux® 21L filters (2.1 m², Gambro Lundia AB) which are based on a blend of polyarylethersulfone (PAES), polyvinylpyrrolidone (PVP) and polyamide and have a wall thickness of 50 µm and an inner diameter of 215 µm. The hollow fibers were assembled in standardized mini-modules according to Example 2 for further tests.

1.26 Comparative Example: Low-Flux Membrane b

Membrane b (FIG. 2) refers to hollow fiber membranes which were extracted from an APS 21E hemodialyzer (2.1 m², Asahi Kasei Medical Co., Ltd.). The hollow fiber membranes are polysulfone based membranes with a wall thickness of 45 µm and an inner diameter of 200 µm. The hollow fibers were used for preparing standardized mini-modules according to Example 2 for further tests.

1.27 Comparative Example: Low-Flux Membrane c

Membrane c (FIG. 2) refers to hollow fiber membranes which were extracted from an APS 21EL hemodialyzer (2.1 m², Asahi Kasei Medical Co., Ltd.). The hollow fiber membranes are polysulfone based membranes with a wall thickness of 45 µm and an inner diameter of 200 µm. The hollow fibers were used for preparing standardized mini-modules according to Example 2 for further tests.

1.28 Comparative Example: Protein Leaking Membrane

The protein leaking membrane (FIG. 2, (▼)) refers to hollow fiber membranes which were extracted from an Filtryzer BK-1.6F filter (1.6 m² from Toray Industries, Inc.) which comprises a so-called PMMA membrane (poly(m-ethyl methacrylate)) having a wall thickness of 30 µm and an inner diameter of 210 µm. The hollow fibers were used for preparing standardized mini-modules according to Example 2 for further tests.

Example 2

Preparation of Filters, Hand Bundles and Mini-Modules; Measurement of Sieving Coefficients 2.1 Preparation of Filter, Hand-Bundles and Mini-Modules Filters can be prepared by introducing a fiber bundle into a dialyser housing. The bundle is potted with polyurethane, ends are cut, on both sides of the dialyser a header is fixed to the housing, the dialyser is rinsed with hot water and dried with air. During this last drying step, a certain amount of about between 10 g and 30 g of residual water per m² effective membrane area is left on the dialyser. After labelling and packaging, the dialyser can be steam-sterilized within the packaging in an autoclave at 121° C. for at least 21 min.

The preparation of a hand bundle after the spinning process is necessary to prepare the fiber bundle for following performance tests with mini-modules. The first process step is to cut the fiber bundles to a defined length of 23 cm. The next process step consists of melting the ends of the fibers. An optical control ensures that all fibers are well melted. Then, the ends of the fiber bundle are transferred into a potting cap. The potting cap is fixed mechanically and a potting tube is put over the potting caps. Then the fibers are potted with polyurethane. After the polyurethane has hardened, the potted membrane bundle is cut to a defined length and stored dry.

Mini-modules (fiber bundles in a housing) are prepared in a similar manner. The mini-modules ensure protection of the fibers and can be used for steam-sterilization. The manufacturing of the mini-modules comprises the following specific steps:

(A) The number of fibers required is calculated for a nominal surface A of 360 cm² according to the following equation:

$$A = \pi \times d_i \times l \times n,$$

wherein $d_i$ is the inner diameter of fiber [cm], n represents the amount of fibers, and l represents the fiber length in the housing (17 cm).

(B) The fiber bundle is cut to a defined length.

(C) The fiber bundle is transferred into the housing before the melting process.

2.2 Albumin, β2-M and Myoglobin Sieving Coefficients

Middle molecules, consisting mostly of peptides and small proteins with molecular weights in the range of 500-60,000 Da, accumulate in renal failure and contribute to the uremic toxic state. Beta2-microglobulin (beta2-MG or β2-M) with a molecular weight of 11,000 is considered representative of these middle molecules. Myoglobin has a molecular weight (MW) of about 17 kDaa is already larger and will not be cleared from blood to the same extend by known high-flux dialyzers, whereas it is readily removed by high cut-off dialyzers. Finally, albumin with a MW of about 67 kDaa is a key element in describing the sieving characteristics of membranes, as albumin should not be allowed to pass a membrane for chronic hemodialysis to a significant extent. The sieving coefficients for said proteins were determined for Membrane A according to the invention, Membrane 6, and for Membrane β according to EN1283 ($Q_B$max, UF=20%) in bovine plasma at with $Q_B$=600 ml/min and UF=120 ml/min. Further measurements were carried out at $Q_B$=400 ml/min and UF=25 ml/min according to DIN EN ISO8637:2014. The bovine plasma used had a total protein concentration of 60±2 g/l. Myoglobin from horse heart (M1882) was purchased from Sigma-Aldrich Co. LLC. Purified β2-M (PHP135) was obtained from Bio-Rad AbD Serotec GmbH or Lee Bio Solutions (St Louis, MO, U.S.A.) and diluted in bovine plasma. The resulting test solutions had the following final concentrations: albumin as contained in the bovine plasma, myoglobin (100 mg/l), β2-M (3 mg/l). The test solutions were gently stirred at 37±1° C. Mini-modules as described in Example 2.1 were primed with 0.9% NaCl solution. The setup for the test was according to ISO 8637:2014. The final protein concentration of the test solution was 60±5 g/l.

Example 3

Dextran Sieving Measurements
3.1 Dextran Solutions

Fractions of dextran supplied by Fluka (Mw 6, 15-20, 40, 70, 100, 200, 500 kDaa) and Sigma-Aldrich (Mw 9-11 kDaa) (both from Sigma-Aldrich Co. LLC, St. Louis, USA) were used without further purification. Solutions of dextrans with the different molecular weight fractions were combined in Millipore water (i.e., Type 1 ultrapure water, as defined by ISO 3696) at a concentration of 1 g/l for each fraction, which results in an overall concentration of 8 g/l.

3.2 Devices and Sample Preparation

For characterizing the membranes according to the invention and comparing them with membranes known from the prior art, it was necessary to eliminate the differences between devices caused by having different membrane surface areas or fiber numbers. Therefore, standardized mini-modules with a surface area of from 280 cm² to 300 cm² were manufactured from the membranes according to the invention or from membranes according to the prior art. In cases where the prior art membranes were part of complete filter devices, the membrane was extracted from said devices and mini-modules were prepared therefrom. Each mini-module had a nominal length of 170 mm, an effective length of approx. 120 mm to 150 mm (without PU potting) and an inner diameter of 10 mm. The internal diameter of fibers ranged between 170 µm and 220 µm, and the wall thickness between 30 µm and 50 µm (depending on the specific membranes used, see Examples 1.1-1.28 for details). Hence, the packing density also varied between 23% and 31%. All mini-modules were immersed in water for 30 min before the filtration experiments. Mini-modules to be characterized after contact with blood first have to be perfused with blood (bovine, 32% of hematocrits, 60 g/l of protein content and 1600 units/l of heparin) for 40 min and rinsed afterwards with water for 30 to 60 min, as proposed elsewhere (Kunas G A, Burke R A, Brierton M A, Ofsthun N J. The effect of blood contact and reuse on the transport properties of high-flux dialysis membranes. ASAIO J. 1996; 42(4):288-294).

3.3 Dextran Sieving Coefficient Tests

Figure 3:
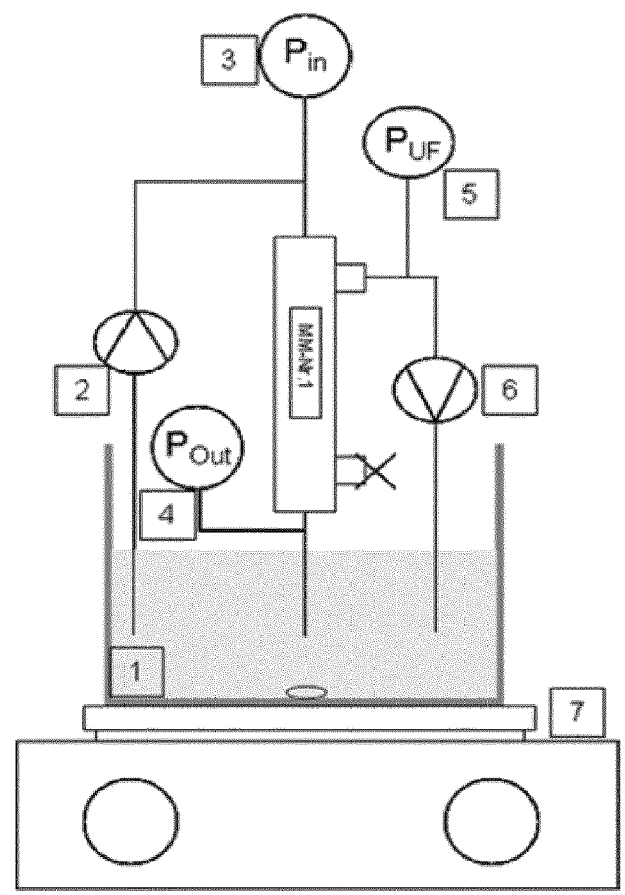
FIG. 3 is a schematic representation of the experimental setup for the filtration experiments according to Example 3, showing: (1) pool with dextran solution, (2) feed pump, (3) manometer, feed side Pin, (4) manometer, retentate side Pout, (5) manometer, filtrate side PUF, (6) filtrate pump (with less than 10 ml/min), (7) heating/stirring plate.

Filtration experiments were carried out under a constant shear rate ($\gamma=750s^{-1}$) and with the ultrafiltration rate set at 20% of the blood side entrance flux $Q_{Bin}$, calculated as:

$$Q_{Bin} = \frac{\gamma \cdot n \cdot \pi \cdot d_i^3 \cdot 60}{32}$$

where $Q_{Bin}$ is the flux at the blood side entrance in ml/min; n is the number of fibers in the minimodule; d: is the inner diameter of the fibers in cm and $\gamma$ is the constant shear rate mentioned above. A scheme of the experimental setup is shown in FIG. 3. As can be seen, the filtration conditions are without backfiltration, contrary to the conditions typical of hemodialysis. Additionally, the chosen conditions assure a filtration regime since the Peclet-number for all the investigated membranes is well above 3 even for molecules in the 0.1 kDaa to 1 kDaa range. The dextran solution was recirculated at 37° C.±1° C. Feed (blood side entrance), retentate (blood side exit), and filtrate (dialysate exit) samples were taken after 15 min. Relative concentration and molecular weight of the samples were analyzed via gel permeation chromatography. The analysis was carried out in a High Performance Liquid Chromatography (HPLC) device (HP 1090A or Agilent 1200; Agilent, Santa Clara, CA, USA) equipped with an RI detector (G1362 from Agilent) and TSKgel columns (PWXL-Guard Column, G 3000 PWXL, G 4000 PWXL; Tosoh, Tessenderlo, Belgium). Samples were filtered through a 0.45 µm filter type OE67 from Schleicher and Schnell, Einbeck, Germany. Calibration was done against dextran standards (Fluka). The sieving coefficient SC is calculated according to the equation as follows:

$$SC = \frac{2 \cdot c_F}{c_P + c_R}$$

where $c_F$ is the concentration of the solute in the filtrate, $c_P$ its concentration in the permeate and $c_R$ its concentration in the retentate.

3.4 Results of the Dextran Sieving Coefficient Tests

TABLE III

MWCO and MWRO values

| Membrane | Classification | Average MWRO (90%) MW [D] | MWCO (10%) MW [D] |
|---|---|---|---|
| Membrane A[1] (Ex. 1.1) | Invention | 11.700 | 75.000 |
| Membrane B[2] (Ex. 1.2) | Invention | 10.700 | 80.000 |
| Membrane C[3] (Ex. 1.3) | Invention | 9.500 | 70.000 |
| Membrane D (Ex. 1.4) | Invention | 11.600 | 88.000 |
| Membrane E (Ex. 1.5) | Invention | 11.700 | 90.000 |
| Membrane F (Ex. 1.6) | Invention | 11.921 | 105.000 |
| Membrane G (Ex. 1.7) | Invention | 10.223 | 71.000 |
| Comparative Example Membrane β (Ex. 1.8) | High cut-off | 15.000 | 300.000 |
| Comparative Example Membrane α (Ex. 1.9) | High cut-off | 19.300 | 200.000 |
| Comparative Example Membrane γ (Ex. 1.10) | High cut-off | 17.000 | 300.000 |
| Comparative Example Membrane ϕ (Ex. 1.11) | High cut-off | 12.020 | 150.000 |
| Comparative Example Membrane 1 (Ex. 1.12) | High-flux | 9.700 | 50.500 |
| Comparative Example Membrane 2 (Ex. 1.13) | High-flux | 6.600 | 33.000 |
| Comparative Example Membrane 3 (Ex. 1.14) | High-flux | 7.300 | 67.000 |
| Comparative Example Membrane 4 (Ex. 1.15) | High-flux | 5.800 | 28.000 |
| Comparative Example Membrane 5 (Ex. 1.16) | High-flux | 4.400 | 18.900 |
| Comparative Example Membrane 6 (Ex. 1.17) | High-flux | 5.300 | 43.000 |
| Comparative Example Membrane 7 (Ex. 1.18) | High-flux | 8.300 | 30.000 |
| Comparative Example Membrane 8 (Ex. 1.19) | High-flux | 7.000 | 32.600 |
| Comparative Example Membrane 9 (Ex. 1.20) | High-flux | 5.800 | 58.000 |
| Comparative Example Membrane 10 (Ex. 1.21) | High-flux | 8.300 | 45.000 |
| Comparative Example Membrane 11 (Ex. 1.22) | High-flux | 5.900 | 50.000 |
| Comparative Example Membrane 12 (Ex. 1.23) | High-flux | 7.300 | 40.000 |

TABLE III-continued

MWCO and MWRO values

| Membrane | Membrane Classi-fication | Average MWRO (90%) MW [D] | Average MWCO (10%) MW [D] |
|---|---|---|---|
| Comparative Example Membrane 13 (Ex. 1.24) | High-flux | 8.700 | 58.000 |
| Comparative Example Membrane a (Ex. 1.25) | Low-flux | 2.200 | 19.000 |
| Comparative Example Membrane b (Ex. 1.26) | Low-flux | 3.060 | 13.000 |
| Comparative Example Membrane c (Ex. 1.27) | Low-flux | 2.790 | 10.000 |
| Comparative Example Protein Leaking Membrane (Ex. 1.28) | Protein Leaking | 3.000 | 67.000 |

[1])Stokes-Einstein pore radius, based on dextran sieving experiments before blood contact: 6.5 ± 0.2 nm
[2])Stokes-Einstein pore radius, based on dextran sieving experiments before blood contact:: 6.0 ± 0.3 nm
[3])Stokes-Einstein pore radius, based on dextran sieving experiments before blood contact:: 5.4 ± 0.1 nm Example 4

Clearance Performance

Figure 4A:
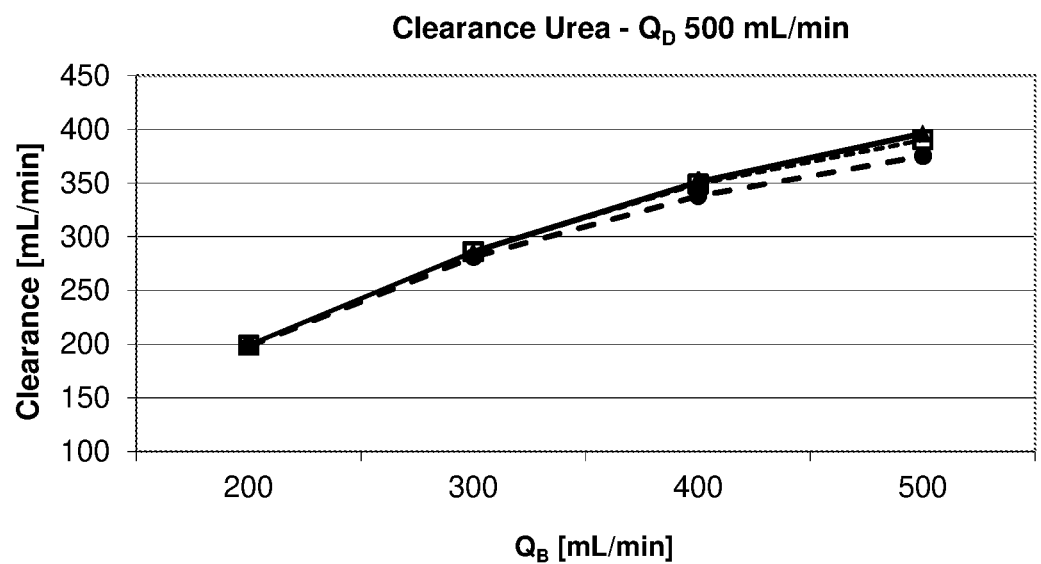
FIG. 4 exemplarily shows clearance curves for urea (FIG. 4A) and for myoglobin (FIG. 4B). See also Table V. Clearances are shown at UF=0 ml/min for a hemodialyzer according to the present invention based on Membrane A (1.7 m², —▲—), a high flux dialyzer based on Membrane 6 (1.8 m², ---●---) and a hemodialyzer based on Membrane β (2.1 m², ⋯□⋯).
Figure 4B:
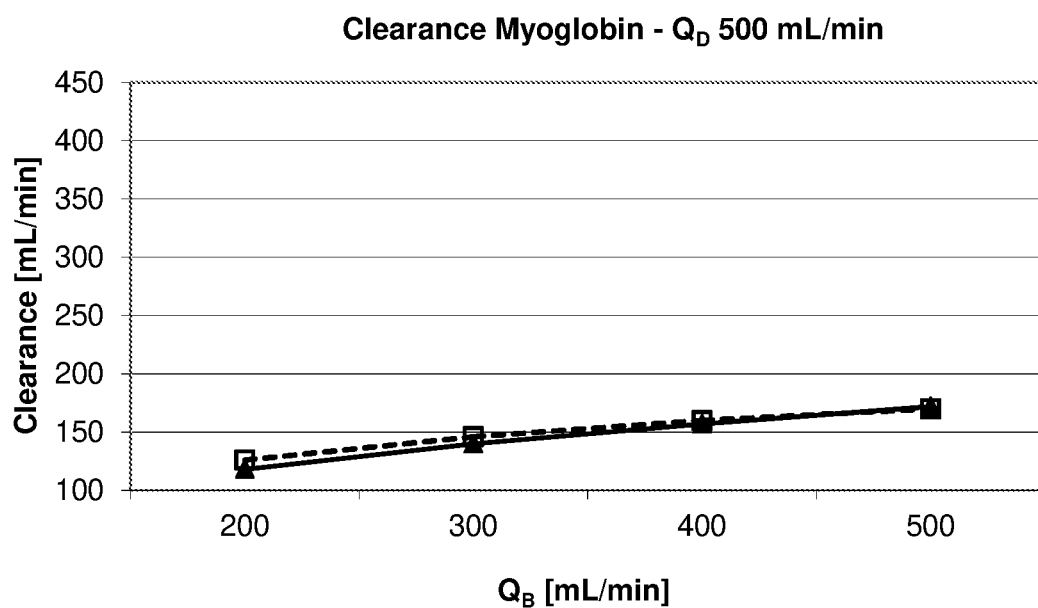
Figure 5A:
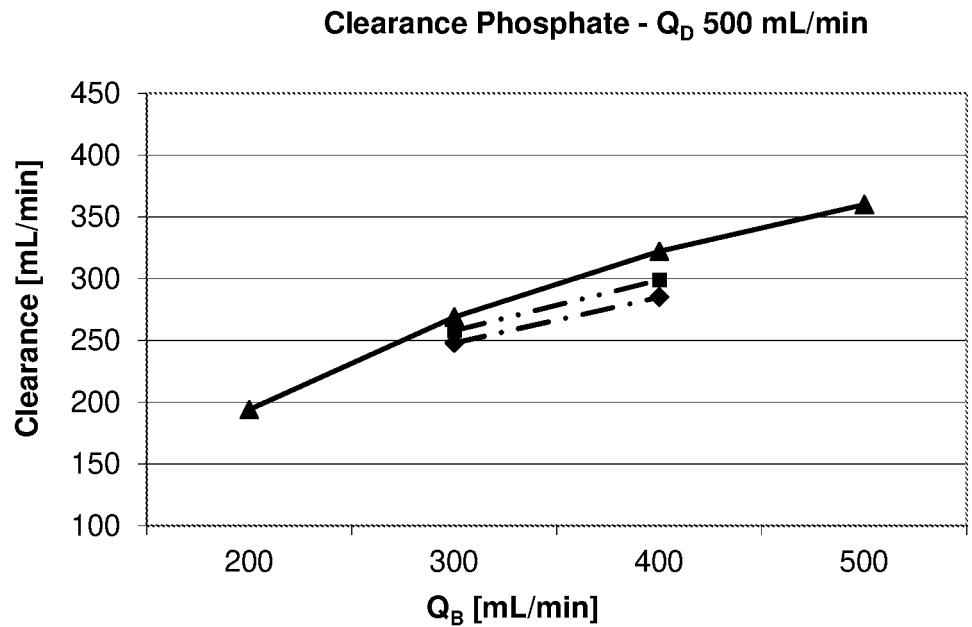
FIG. 5 exemplarily shows clearance curves for phosphate (FIG. 5A) and for cytochrome C (FIG. 5B). See also Table VI. Clearances are shown at UF=0 ml/min for a hemodialyzer according to the present invention based on Membrane A (1.7 m², —▲—), $FX_{CorDiax}80$ (1.8 m², —◆—) and $FX_{CorDiax}100$ (2.2 m², ⋯■⋯) in hemodialysis mode.
Figure 5B:
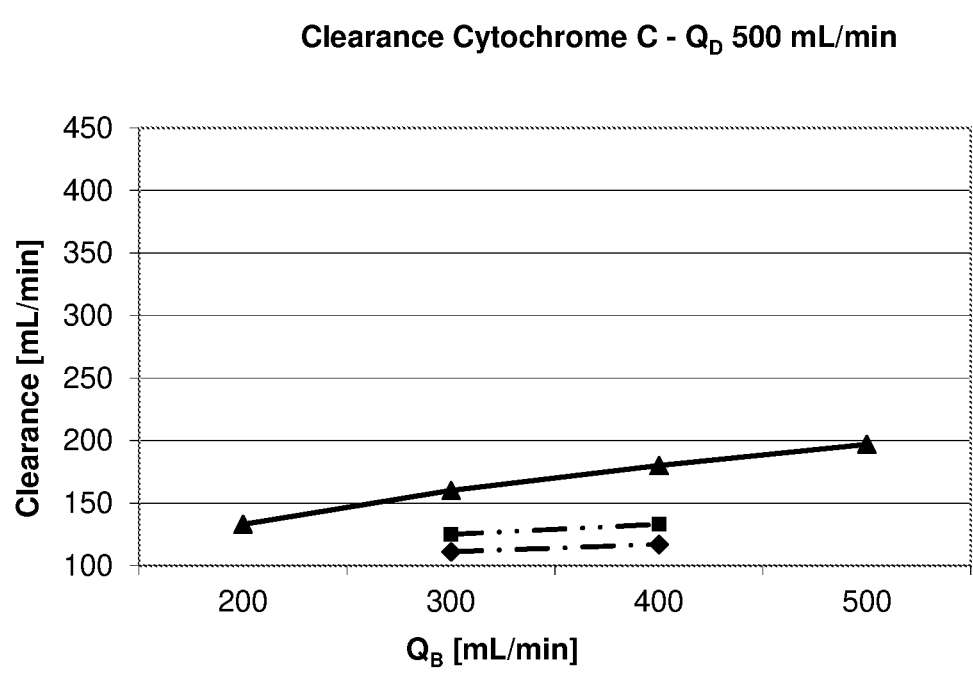
Figure 6A:
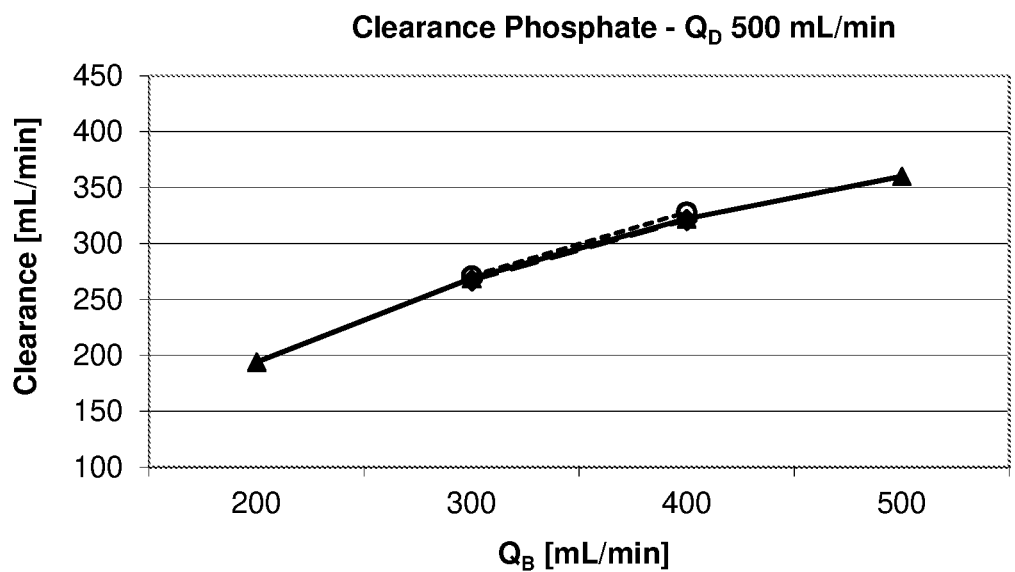
FIG. 6 exemplarily shows clearance curves for phosphate (FIG. 6A) and for cytochrome C (FIG. 6B). See also Table VII. Clearances are shown at UF=0 ml/min for a hemodialyzer according to the present invention based on Membrane A (1.7 m², —▲—), and for $FX_{CorDiax}800$ (2.0 m², —◆—) and $FX_{CorDiax}1000$ (2.3 m², ⋯■⋯) at UF=75 ml/min and UF=100 ml/min, respectively.
Figure 6B:
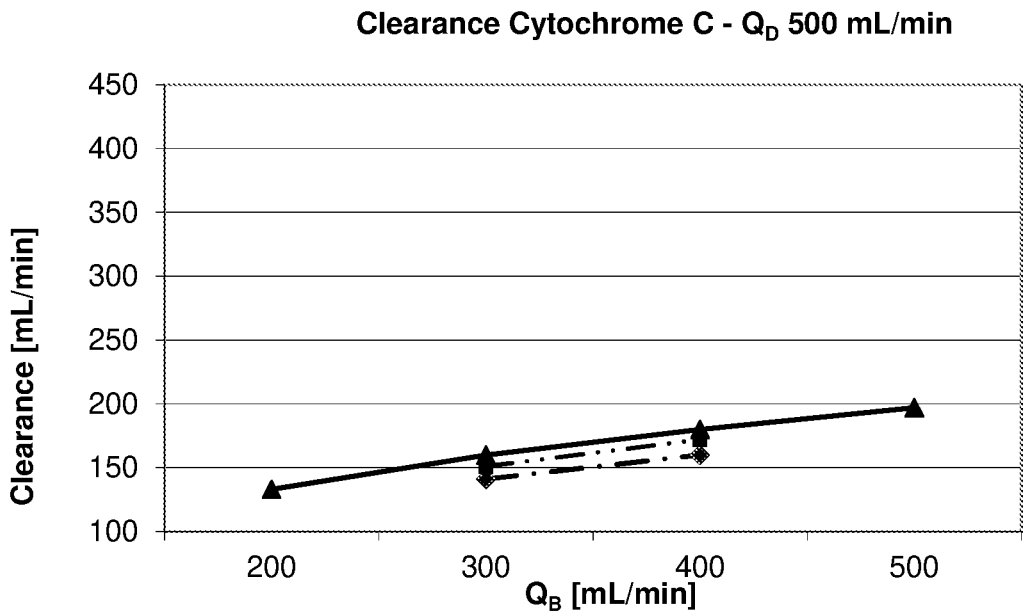
Figure 7A:
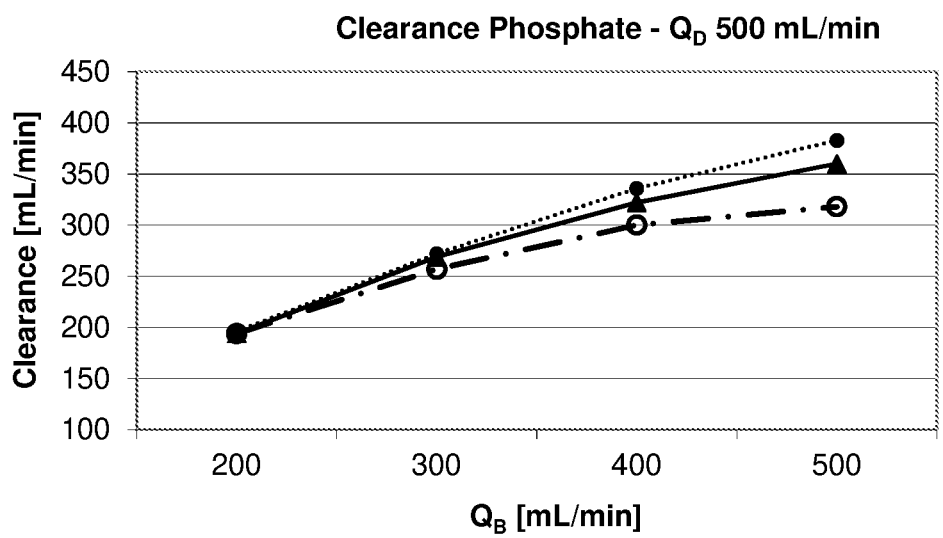
FIG. 7 exemplarily shows clearance curves for phosphate (FIG. 7A) and for cytochrome C (FIG. 7B). See also Table VIII. Clearances are shown at UF=0 ml/min for a hemodialyzer according to the present invention based on Membrane A (1.7 m², —▲—), and hemodiafilters (Nephros OLpūr™ MD 220 (2.2 m², ⋯●⋯) and Nephros OLpūr™ MD 190 (1.9 m², —○—), with $Q_s$=200 ml/min, corresponding to an UF of 200 ml/min.
Figure 7B:
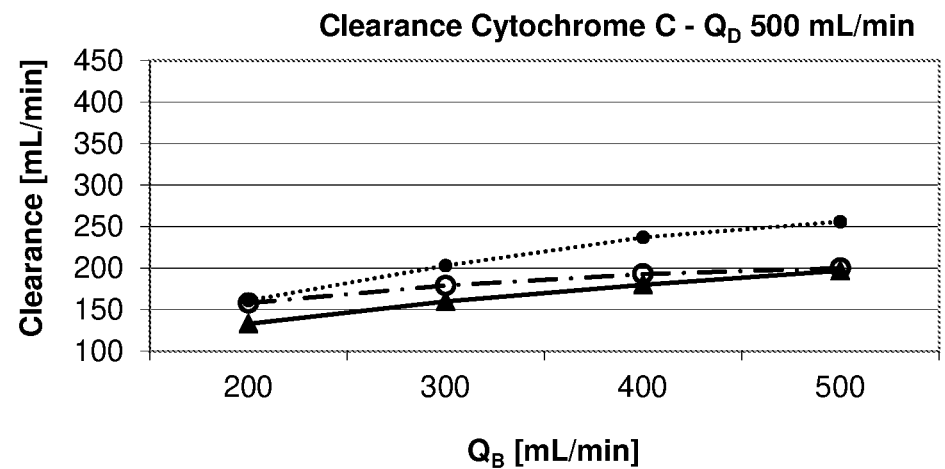
Figure 8A:
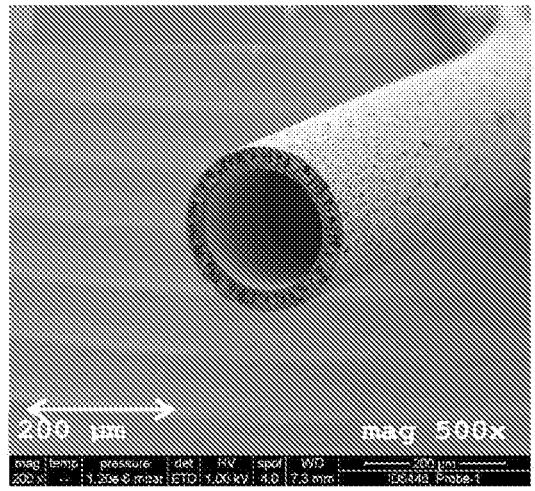
FIG. 8A to F exemplarily show scanning electron micrographs of Membrane A according to the invention. Magnifications used are indicated in each Figure.
Figure 8B:
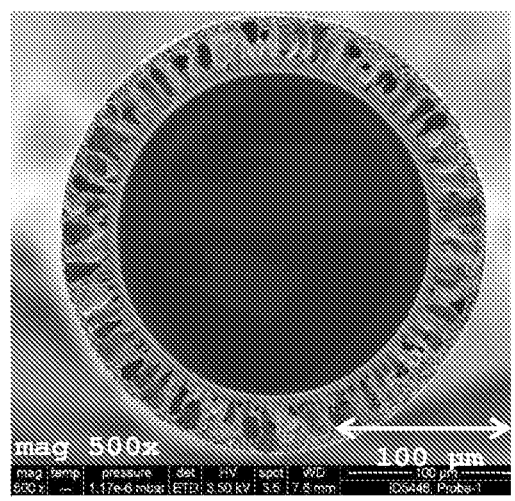
Figure 8C:
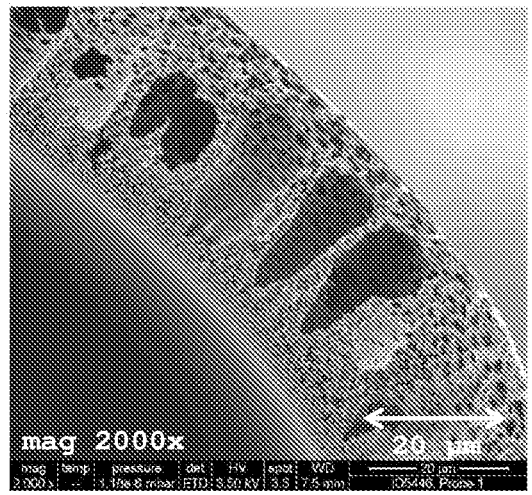
Figure 8D:
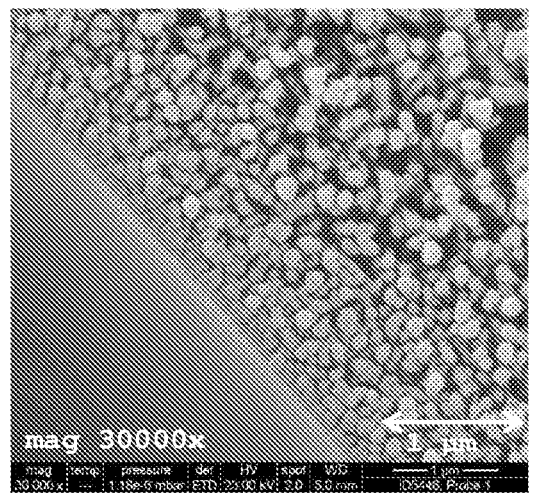
Figure 8E:
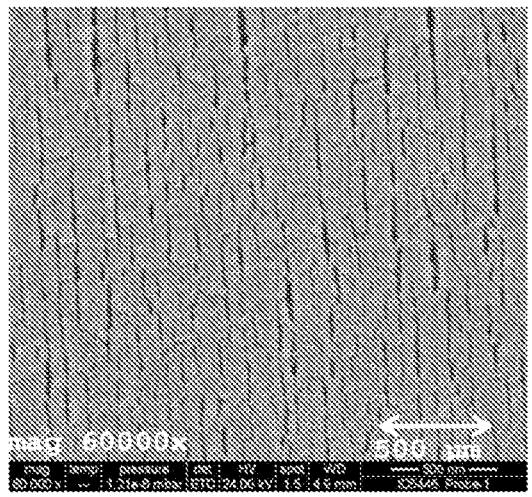
Figure 8F:
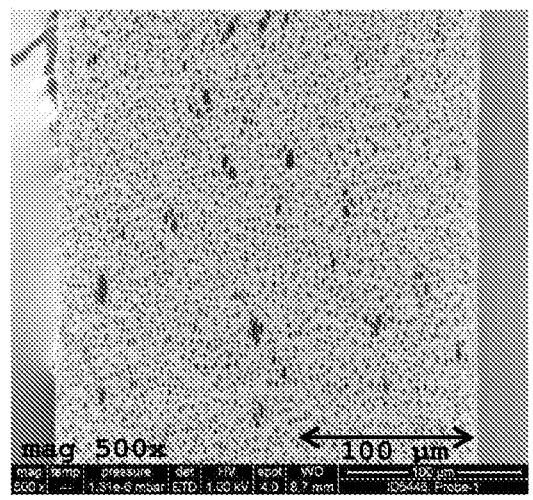
Figure 9A:
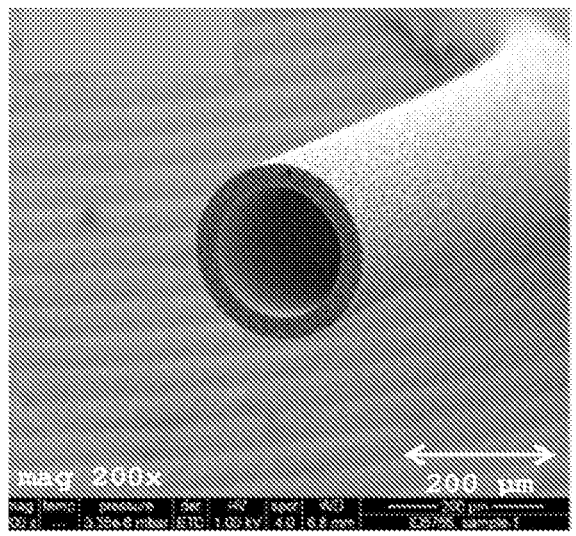
FIG. 9A to F exemplarily show scanning electron micrographs of Membrane F according to the invention. Magnifications used are indicated in each Figure.
Figure 9B:
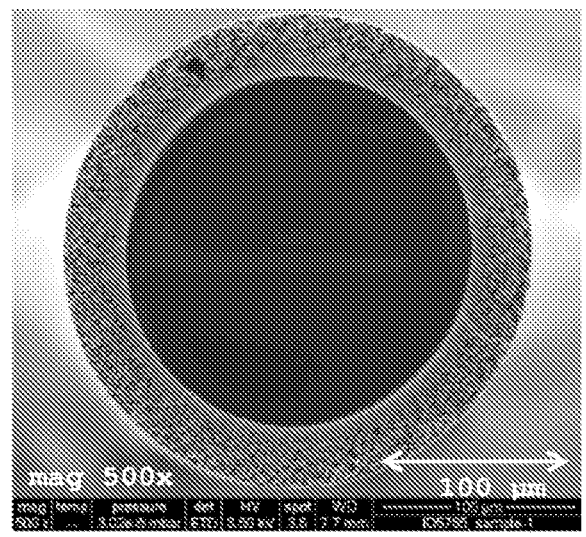
Figure 9C:
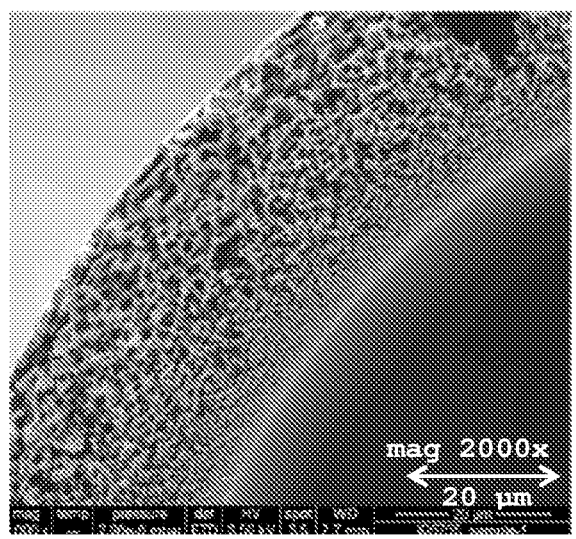
Figure 9D:
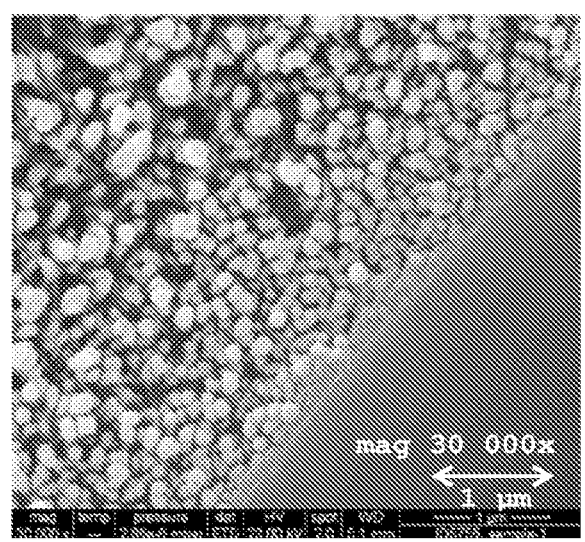
Figure 9E:
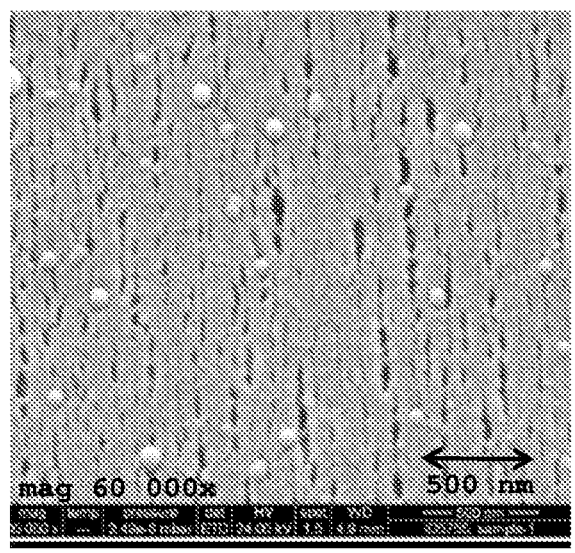
Figure 9F:
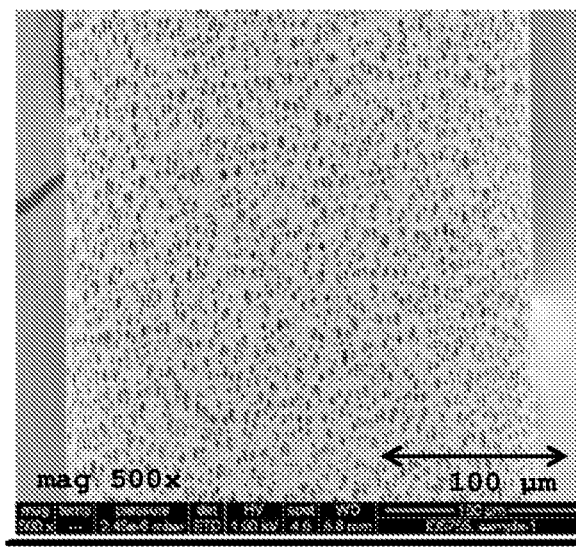

The clearance C (ml/min) refers to the volume of a solution from which a solute is completely removed per unit time. In contrast to the sieving coefficient which is the best way to describe a membrane as the essential component of a hemodialyzer, clearance is a measure of the overall dialyzer function and hence dialysis effectiveness. If not indicated otherwise, the clearance performance of a dialyzer was determined according to ISO 8637:2004(E). The set-up of the test circuit was as shown in FIG. 4 of ISO 8637:2004(E). Flows are operated in single path.

Filters were prepared from Membrane A with an effective surface area of 1.7 m² (12996 fibers, all ondulated) and compared with a filter prepared from a high cut-off membrane, Membrane β (2.1 m², all ondulated), with a filter prepared from a standard high-flux membrane, Membrane 6 (1.8 m², all ondulated) (Table V), and with high-flux dialyzers $FX_{CorDiax}80$ (1.8 m²) and $FX_{CorDiax}100$ (2.2 m²) (Table VI), both from Fresenius Medical Care Deutschland GmbH. Comparison of said filters was done in hemodialysis mode.

Membrane A was also compared with Nephros OLpūr™ MD 190, Nephros OLpūr™ MD 220 (1.9 m² and 2.2. m², respectively, both from Nephros Inc. U.S.A.) and FX Cor-Diax Heamodiafilters $FX_{CorDiax}800$ and $FX_{CorDiax}1000$, wherein clearance values for the Nephros and FX filters were determined in hemodiafiltration mode (see Tables VII and VIII) in order to compare outcomes for the membrane according to the invention in hemodialysis mode with the outcome of filters designed for HDF in hemodiafiltration mode.

In each case, the blood compartment of the tested device was perfused with dialysis fluid containing one or more of the test substances as indicated in Table IV. The dialysate compartment was perfused with dialysate.

TABLE IV

Concentration of test substances in the test solutions used for determining clearance rates

| Test Substance (MW [Da]) | Concentration |
|---|---|
| Urea (60) | 17 mmol/l |
| Creatinine (113) | 884 µmol/l |

TABLE IV-continued

Concentration of test substances in the test solutions used for determining clearance rates

| Test Substance (MW [Da]) | Concentration |
|---|---|
| Phosphate (132) | 3.16 mmol/l |
| Vitamin B12 (1355) | 37 µmol/l |
| Inulin (5200) | 0.10 g/l |
| Cytochrome C (12230) | 0.03 g/l |
| Myoglobin (17000) | 6 µmol/l |

Stable blood and dialysate flow rates were established as indicated in the respective examples shown in Tables V, VI, VII and VIII. Temperature (37° C.±1), pressures and ultrafiltration rates were also kept stable as indicated. Test samples were collected not earlier than 10 minutes after a steady state had been reached. The samples were analyzed and the clearance was calculated according to formula (I).

$$C = \frac{C_{Bin} - C_{Bout}}{C_{Bin}} Q_{Bin} + \frac{C_{Bout}}{C_{Bout}} Q_F \qquad (I)$$

where $C_{Bin}$ is the concentration of solute on the blood inlet side of the hemodialyser;

$C_{Bout}$ is the concentration of solute on the blood outlet side of the hemodialyser;

$Q_{Bin}$ is the blood flow rate at the inlet of the device; and $O_P$ is the filtrate flow rate (ultrafiltration rate).

TABLE V

Clearance performance of hemodialyzers according to the invention (based on Membrane A) in comparison with hemodialyzers of the prior art (hemodialysis mode)

| | Clearance (mL/min) in vitro | | |
|---|---|---|---|
| | $Q_D$ = 500 ml/min | | $Q_D$ = 500 ml/min |
| QB [ml/min] | Membrane 6 filter device (1.8 m² UF = 0 ml/min) | Membrane β filter device (2.2 m² UF = 0 ml/min) | Membrane A filter device (1.7 m² UF = 0 ml/min) |
| | Urea | | |
| 200 | 198 | 199 | 199 |
| 300 | 281 | 286 | 286 |
| 400 | 338 | 349 | 351 |
| 500 | 375 | 390 | 396 |
| | Creatinine | | |
| 200 | 195 | 196 | 196 |
| 300 | 267 | 273 | 273 |
| 400 | 315 | 326 | 329 |
| 500 | 348 | 361 | 369 |
| | Phosphate | | |
| 200 | 191 | 195 | 194 |
| 300 | 255 | 269 | 269 |
| 400 | 297 | 320 | 322 |
| 500 | 326 | 354 | 360 |
| | Vitamin $B_{12}$ | | |
| 200 | 158 | 175 | 170 |
| 300 | 191 | 221 | 216 |
| 400 | 213 | 252 | 249 |
| 500 | 228 | 274 | 276 |

TABLE V-continued

Clearance performance of hemodialyzers according to the invention (based on Membrane A) in comparison with hemodialyzers of the prior art (hemodialysis mode)

| | Clearance (mL/min) in vitro | | |
|---|---|---|---|
| | $Q_D$ = 500 ml/min | | $Q_D$ = 500 ml/min |
| QB [ml/min] | Membrane 6 filter device (1.8 m²) UF = 0 ml/min | Membrane β filter device (2.2 m²) UF = 0 ml/min | Membrane A filter device (1.7 m²) UF = 0 ml/min |
| | Inulin | | |
| 200 | — | 157 | 141 |
| 300 | — | 191 | 171 |
| 400 | — | 214 | 194 |
| 500 | — | 230 | 213 |
| | Myoglobin | | |
| 200 | — | 126 | 118 |
| 300 | — | 146 | 140 |
| 400 | — | 160 | 157 |
| 500 | — | 170 | 172 |

TABLE VI

Clearance performance of hemodialyzers according to the invention (based on Membrane A) in comparison with hemodialyzers of the prior art (hemodialysis mode)

| | Clearance (ml/min) in vitro | | |
|---|---|---|---|
| | $Q_D$ = 500 ml/min | | $Q_D$ = 500 ml/min |
| QB [ml/min] | FX$_{CorDiax}$80 (1.8 m²) UF = 0 ml/min | FX$_{CorDiax}$100 (2.2 m²) UF = 0 ml/min | Membrane A filter device (1.7 m²) UF = 0 ml/min |
| | Urea | | |
| 200 | — | — | 199 |
| 300 | 280 | 283 | 286 |
| 400 | 336 | 341 | 351 |
| 500 | — | — | 396 |
| | Creatinine | | |
| 200 | — | — | 196 |
| 300 | 261 | 272 | 273 |
| 400 | 303 | 321 | 329 |
| 500 | — | — | 369 |
| | Phosphate | | |
| 200 | — | — | 194 |
| 300 | 248 | 258 | 269 |
| 400 | 285 | 299 | 322 |
| 500 | — | — | 360 |
| | Vitamin B$_{12}$ | | |
| 200 | — | — | 170 |
| 300 | 190 | 207 | 216 |
| 400 | 209 | 229 | 249 |
| 500 | — | — | 276 |
| | Cytochrome C | | |
| 200 | — | — | 133 |
| 300 | 111 | 125 | 160 |
| 400 | 117 | 133 | 180 |
| 500 | — | — | 197 |

TABLE VII

Clearance performance of hemodialyzers according to the invention (based on Membrane A) in hemodialysis mode in comparison with hemodiafilters of the prior art (hemodiafiltration mode)

| | Clearance (ml/min) in vitro | | |
|---|---|---|---|
| | $Q_D$ = 500 ml/min | | $Q_D$ = 500 ml/min, UF = 0 ml/min |
| QB [ml/min] | FX$_{CorDiax}$800 (2.0 m²) UF = 75 mL/min* UF = 100 mL/min# | FX$_{CorDiax}$1000 (2.3 m²) UF = 75 mL/min* UF = 100 mL/min# | Membrane A filter device (1.7 m²) UF = 0 mL/min |
| | Urea | | |
| 200 | — | — | 199 |
| 300 | 291* | 292* | 286 |
| 400 | 365# | 367# | 351 |
| 500 | — | — | 396 |
| | Creatinine | | |
| 200 | — | — | 196 |
| 300 | 277 | 280 | 273 |
| 400 | 339 | 343 | 329 |
| 500 | — | — | 369 |
| | Phosphate | | |
| 200 | — | — | 194 |
| 300 | 267 | 271 | 269 |
| 400 | 321 | 328 | 322 |
| 500 | — | — | 360 |
| | Vitamin B$_{12}$ | | |
| 200 | — | — | 170 |
| 300 | 217* | 225* | 216 |
| 400 | 251# | 262# | 249 |
| 500 | — | — | 276 |
| | Cytochrome C | | |
| 200 | — | — | 133 |
| 300 | 141 | 151 | 160 |
| 400 | 160 | 172 | 180 |
| 500 | — | — | 197 |

TABLE VIII

Clearance performance of hemodialyzers according to the invention (based on Membranes A and B) in hemodialysis mode in comparison with hemodiafilters of the prior art (hemodiafiltration mode)

| | Clearance (mL/min) in vitro | | | |
|---|---|---|---|---|
| | $Q_D$ = 500 ml/min | | $Q_D$ = 500 ml/min, | $Q_D$ = 500 ml/min |
| QB [ml/min] | Nephros OLpur™ MD 190 (1.9 m² UF = 200 ml/min) | Nephros OLpur™ MD 220 (2.2 m² UF = 200 ml/min) | Membrane A filter device (1.7 m² UF = 0 ml/min) | Membrane B filter device (2.0 m² UF = 0 ml/min) |
| | Urea | | | |
| 200 | 198 | 199 | 199 | — |
| 300 | 276 | 291 | 286 | — |
| 400 | 332 | 364 | 351 | 360** |
| 500 | 353 | 424 | 396 | — |
| | Creatinine | | | |
| 200 | 196 | 198 | 196 | — |
| 300 | 264 | 279 | 273 | — |
| 400 | 311 | 348 | 329 | — |
| 500 | 331 | 403 | 369 | — |

TABLE VIII-continued

Clearance performance of hemodialyzers according to the invention (based on Membranes A and B) in hemodialysis mode in comparison with hemodiafliters of the prior art (hemodiafiltration mode)

| | Clearance (mL/min) in vitro | | | |
|---|---|---|---|---|
| | $Q_D$ = 500 ml/min | $Q_D$ = 500 ml/min | $Q_D$ = 500 ml/min, | $Q_D$ = 500 ml/min |
| QB [ml/min] | Nephros OLpūrTM MD 190 (1.9 m² UF = 200 ml/min) | Nephros OLpūrTM MD 220 (2.2 m² UF = 200 ml/min) | Membrane A filter device (1.7 m² UF = 0 ml/min) | Membrane B filter device (2.0 m² UF = 0 ml/min) |
| | Phosphate | | | |
| 200 | 194 | 196 | 194 | — |
| 300 | 257 | 272 | 269 | — |
| 400 | 300 | 336 | 322 | — |
| 500 | 318 | 383 | 360 | — |
| | Vitamin $B_{12}$ | | | |
| 200 | 191 | 192 | 170 | — |
| 300 | 221 | 247 | 216 | — |
| 400 | 242 | 292 | 249 | 260** |
| 500 | 251 | 323 | 276 | — |
| | Cytochrome C | | | |
| 200 | 158 | 161 | 133 | — |
| 300 | 179 | 203 | 160 | — |
| 400 | 193 | 237 | 180 | — |
| 500 | 200 | 256 | 197 | — |

**constructed value

Example 5

Determination of Albumin Loss in a Simulated Treatment

The simulated treatment is performed, for example, with a AK 200™ S dialysis machine. During the treatment samples of 1 ml are secured from the dialysate side of the system after 15, 30, 45, 60, 90, 120, 150, 180, 210 and 240 minutes and the albumin concentration in the samples in mq/l is determined (BSA, Bovine Serum Alubmin). Albumin loss is calculated with the help of SigmaPlot software by establishing a regression curve of the type $f(x)=y_o+ae^{-bx}$. The albumin loss can be calculated by integration of the regression curve, $F_{(x)}$ from 0 to 240 minutes, i.e. $F(x)=bxy_o-ae^{-bx}$.

The simulated treatment is carried out as follows. A bag with 0.9% NaCl (500 ml) is connected to the dialysis monitor. The blood pump is started and the test filter is rinsed at $Q_B$=100 ml/min, $Q_D$=700 ml/min, UF-0.1 ml/min with the said sodium chloride solution. Afterwards, the dialyzer is filled by using the prescribed dialysate flow. The bovine blood (5000±50 ml) is provided in a container and placed in a water bath at 38±1° C. 5 ml of heparin are added in the beginning and then every hour. The blood is carefully stirred throughout the treatment. The test can be run in HD or HDF mode. Standard parameters are $Q_B$=400 ml/min, $Q_D$=500 ml/min, UF=−10. In case UF is >0 ml/min substitution fluid has to be used. Blood flow, dialysate flow and UF rate are started and samples are taken from the dialysate side at the respective times. Albumin concentration in the samples can be determined according to known methods.

The invention claimed is:

1. A method of purifying blood of a patient, said method comprising the step of using a hemodialyzer on the patient, wherein the hemodialyzer comprises a membrane comprising an asymmetric finger-like structure comprising at least three layers, wherein the first layer is a separation layer, wherein the second layer is a sponge structure, and wherein the third layer is a finger structure,
wherein the membrane comprises i) at least one hydrophobic polymer component and ii) at least one hydrophilic polymer component, wherein the membrane has a molecular retention onset (MWRO) of between 9.0 kDa and 14.0 kDa and a molecular weight cut-off (MWCO) of between 55 kDa and 130 kDa as determined by dextran sieving before blood contact of the membrane, and
wherein the separation layer comprises pores.

2. The method of claim 1, wherein the patient is a patient with acute renal failure.

3. The method of claim 1, wherein the patient is a patient with chronic renal failure.

4. The method of claim 1, wherein the method is performed at a blood flow rate (QB) in the range of from 200 ml/min to 600 ml/min.

5. The method of claim 1, wherein the method is performed at a dialysate flow rate (QD) in the range of from 300 ml/min to 1000 ml/min.

6. The method of claim 1, wherein the method is performed at an ultrafiltration flow rate (UF) in the range of from 0 to 30 ml/min.

7. The method of claim 1, wherein the method is performed at an ultrafiltration flow rate (UF) in the range of from 0 to 15 ml/min.

8. The method of claim 1, wherein the membrane provides an effective surface area in the range of from 1.1 m² to 2.5 m².

9. The method of claim 1, wherein the membrane provides an effective surface area in the range of 1.7 m².

10. The method of claim 1, wherein the hemodialyzer comprises a packing density in the range of from 50% to 65%.

11. The method of claim 1, wherein the pores have an average radius, before blood or plasma contact, between 5.0 nm and 7.0 nm.

12. The method of claim 1, wherein the pores have an average radius, before blood or plasma contact, between 5.0 nm and 6.7 nm.

13. The method of claim 1, wherein the membrane further comprises a fourth layer, wherein the fourth layer is an outer surface.

14. The method of claim 1, wherein the method is performed at a QB between 200 ml/min and 500 ml/min, a QD of 500 ml/min and an UF of 0 ml/min, and wherein the method provides a clearance rate of urea in the range of from between 190 ml/min and 400 ml/min, wherein the clearance rate is determined in vitro according to DIN EN ISO8637:2014.

15. The method of claim 1, wherein the method is performed at a QB between 200 ml/min and 500 ml/min, a QD of 500 ml/min and an UF of 0 ml/min, and wherein the method provides a clearance rate of creatinine in the range of from between 190 ml/min and 380 ml/min, wherein the clearance rate is determined in vitro according to DIN EN ISO8637:2014.

16. The method of claim 1, wherein the method is performed at a QB between 200 ml/min and 500 ml/min, a QD of 500 ml/min and an UF of 0 ml/min, and wherein the method provides a clearance rate of phosphate in the range of from between 190 ml/min and 380 ml/min, wherein the clearance rate is determined in vitro according to DIN EN ISO8637:2014.

17. The method of claim 1, wherein the method is performed at a QB between 200 ml/min and 500 ml/min, a QD of 500 ml/min and an UF of 0 ml/min, and wherein the method provides a clearance rate of vitamin B12 in the range of from between 170 ml/min and 280 ml/min, wherein the clearance rate is determined in vitro according to DIN EN ISO8637:2014.

18. The method of claim 1, wherein the method is performed at a QB between 200 ml/min and 500 ml/min, a QD of 500 ml/min and an UF of 0 ml/min, and wherein the method provides a clearance rate of inulin in the range of from between 140 ml/min and 240 ml/min, wherein the clearance rate is determined in vitro according to DIN EN ISO8637:2014.

19. The method of claim 1, wherein the method is performed at a QB between 200 ml/min and 500 ml/min, a QD of 500 ml/min and an UF of 0 ml/min, and wherein the method provides a clearance rate of myoglobin in the range of from between 110 ml/min and 200 ml/min, wherein the clearance rate is determined in vitro according to DIN EN ISO8637:2014.

20. The method of claim 1, wherein the method is performed at a QB between 200 ml/min and 500 ml/min, a QD of 500 ml/min and an UF of 0 ml/min, and wherein the method provides a clearance rate of cytochrome C in the range of from between 130 ml/min and 200 ml/min, wherein the clearance rate is determined in vitro according to DIN EN ISO8637:2014.

\* \* \* \* \*